United States Patent
de Boever et al.

(10) Patent No.: US 10,683,547 B2
(45) Date of Patent: Jun. 16, 2020

(54) EPIGENETIC MARKERS FOR RESPIRATORY ALLERGY

(71) Applicant: VITO NV, Mol (BE)

(72) Inventors: Patrick de Boever, Mol (BE); Sabine Langie, Mol (BE)

(73) Assignee: VITO NV, Mol (BE)

( * ) Notice: Subject to any disclaimer, the term of this patent is extended or adjusted under 35 U.S.C. 154(b) by 0 days.

(21) Appl. No.: 15/578,174

(22) PCT Filed: May 27, 2016

(86) PCT No.: PCT/EP2016/062017
§ 371 (c)(1),
(2) Date: Nov. 29, 2017

(87) PCT Pub. No.: WO2016/193151
PCT Pub. Date: Dec. 8, 2016

(65) Prior Publication Data
US 2018/0148785 A1    May 31, 2018

(30) Foreign Application Priority Data
May 29, 2015 (EP) .................................... 15169841

(51) Int. Cl.
*C12Q 1/6883* (2018.01)
*C12P 19/34* (2006.01)

(52) U.S. Cl.
CPC ...... *C12Q 1/6883* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

2013/0084287 A1* 4/2013 Shames ................ C12O 1/6827
424/133.1

OTHER PUBLICATIONS

Reinus, PLos One, 2012, 7(7), e41361, p. 1-13.*
Nestor (PLOS Genetics, 2014, vol. 10, e1004059, pp. 1-8).*
Wang et al. (Clinical & Experimental Allergy, 2013, 43, 535-543).*
Furmanski, A.L., et al., Tissue-Derived Hedgehog Proteins Modulate Th Differentiation and Disease, Journal of Immunology 190:2641-2649, Feb. 2013.
Gunawardhana, L.P., et al., Differential DNA Methylation Profiles of Infants Exposed to Maternal Asthma During Pregnancy, Pediatric Pulmonology 49:852-862, 2014.
Perera, F., et al., Relation of DNA Methylation of 5'-CpG Island of ACSL3 to Transplacental Exposure to Airborne Polycyclic Aromatic Hydrocarbons and Childhood Asthma, PLoS One 4(2):1-14, Feb. 2009.
Plenary Symposia, In Vitro Cellular and Developmental Biology—Animal 51(Suppl 1):S2-S4, 2015.
Thompson, T.M., Comparison of Whole-Genome DNA Methylation Patterns in Whole Blood, Saliva, and Lymphoblastoid Cell Lines, Behavior Genetics 43:168-176, 2013.

* cited by examiner

*Primary Examiner* — Sarae L Bausch
(74) *Attorney, Agent, or Firm* — Knobbe, Martens, Olson & Bear LLP

(57) ABSTRACT

A method relates to epigenetic markers and their diagnostic and predictive value for respiratory allergy. The method can include assaying a test sample from the patient for a DNA hypermethylation or hypomethylation of at least GLI2 region, in which hypermethylation or hypomethylation of the gene region in the test sample indicates or predicts a respiratory allergy in the patient.

4 Claims, 7 Drawing Sheets

Table 1

| name | ensembl_gene_id | entrezgene | hgnc_id | unigene | wikigene_id |
|---|---|---|---|---|---|
| RPTOR | ENSG00000141564 | 57521 | 30287 | Hs.133044 | 57521 |
| BLOC1S4 | ENSG00000186222 | 55330 | 24206 | Hs.7570 | 55330 |
| ACBD4 | ENSG00000181513 | 79777 | 23337 | Hs.110298 | 79777 |
| MYT1L | ENSG00000186487 | 23040 | 7623 | Hs.434418\|Hs.669852 | 23040 |
| TMEM80 | ENSG00000177042 | 283232 | 27453 | | 283232 |
| GHRL | ENSG00000157017 | 51738 | 18129 | Hs.590080 | 51738 |
| STOX2 | ENSG00000173320 | 56977 | 25450 | | 56977 |
| DEAF1 | ENSG00000177030 | 10522 | 14677 | Hs.243994 | 10522 |
| CYP26C1 | ENSG00000187553 | 340665 | 20577 | Hs.369993 | 340665 |
| NOSIP | ENSG00000142546 | 51070 | 17946 | Hs.7236 | 51070 |
| CELF6 | ENSG00000140488\|ENSG00000273025 | 60677 | 14059 | Hs.348342 | 60677 |
| ATF3 | ENSG00000162772 | 467 | 785 | | 467 |
| ABAT | ENSG00000183044 | 18 | 23 | Hs.336768\|Hs.739069 | 18 |
| PRDM1 | ENSG00000057657 | 639 | 9346 | Hs.436023 | 639 |
| MAST3 | ENSG00000099308 | 23031 | 19036 | Hs.466184 | 23031 |
| EGFL7 | ENSG00000172889 | 51162 | 20594 | Hs.91481 | 51162 |
| LINC00676 | ENSG00000234854 | 101409253 | 44394 | | 101409253 |
| RTP5 | ENSG00000188011\|ENSG00000277949 | 285093 | 26585 | | 285093 |
| VWA3A | ENSG00000175267 | 101930115\|146177 | 27088 | Hs.10697 | 101930115\|146177 |
| LRCOL1 | ENSG00000204583 | 100507055 | 44160 | | 100507055 |
| RUNX3 | ENSG00000020633 | 864 | 10473 | Hs.170019 | 864 |
| PCNT | ENSG00000160299 | 5116 | 16068 | Hs.474069 | 5116 |
| PDCD1 | ENSG00000188389\|ENSG00000276977 | 5133 | 8760 | Hs.158297 | 5133 |
| PRDM8 | ENSG00000152784 | 56978 | 13993 | Hs.373642 | 56978 |
| HLA-DRA | ENSG00000204287\|ENSG00000206308\|ENSG00000226260\|ENSG00000227993\|ENSG00000228987\|ENSG00000230726\|ENSG00000234794 | 3122 | 4947 | | 3122 |
| TM9SF2 | ENSG00000125304 | 9375 | 11865 | Hs.607896 | 9375 |

Fig. 1

Table 1 (continued)

| LEP | ENSG00000174697 | 3952 | 6553 | Hs.194236 | 3952 |
|---|---|---|---|---|---|
| PON1 | ENSG00000005421 | 5444 | 9204 | Hs.370995 | 5444 |
| TAPBP | ENSG00000112493\|ENSG00000206208\|ENSG00000206281\|ENSG00000231925\|ENSG00000236490\|LRG_114 | 6892 | 11566 | Hs.370937 | 6892 |
| NKAPL | ENSG00000189134 | 222698 | 21584 | Hs.48787 | 222698 |
| CKMT2 | ENSG00000131730 | 1160 | 1996 | Hs.80691 | 1160 |
| GADL1 | ENSG00000144644 | 339896 | 27949 | Hs.657052 | 339896 |
| OSBPL2 | ENSG00000130703 | 400850\|9885 | 15761 | Hs.473254\|Hs.711994\|Hs.734485 | 400850\|9885 |
| NECAB3 | ENSG00000125967 | 63941 | 15851 | Hs.516986 | 63941 |
| NRBP1 | ENSG00000115216 | 29959 | 7993 | Hs.515876\|Hs.738928 | 29959 |
| PARD6G | ENSG00000178184 | 84552 | 16076 | Hs.654920 | 84552 |
| HSF5 | ENSG00000176160 | 124535 | 26862 | Hs.380061 | 124535 |
| SLC12A4 | ENSG00000124067 | 6560 | 10913 | Hs.10094 | 6560 |
| ONECUT1 | ENSG00000169856 | 3175 | 8138 | Hs.658573 | 3175 |
| DDX11 | ENSG00000013573 | 1663 | 2736 | Hs.443960\|Hs.447869 | 1663 |
| GRAMD1B | ENSG00000023171 | 57476 | 29214 | Hs.144725 | 57476 |
| CYP2E1 | ENSG00000130649 | 1571 | 2631 | Hs.12907 | 1571 |
| LINC01475 | ENSG00000257582 | 101927324 | 51113 | Hs.642589 | 101927324 |
| LINC00839 | ENSG00000185904 | 84856 | 28269 | Hs.55977 | 84856 |
| LOC441666 | | | | | |
| GATA3-AS1 | ENSG00000197308 | 399717 | 33786 | Hs.669736 | 399717 |
| PM20D1 | ENSG00000162877 | 148811 | 26518 | Hs.177744 | 148811 |
| PSG4 | ENSG00000243137 | 5672 | 9521 | Hs.711363 | 5672 |
| SMAD3 | ENSG00000166949 | 4088 | 6769 | Hs.727986 | 4088 |
| CUX1 | ENSG00000257923 | 1523 | 2557 | Hs.191482 | 1523 |
| SLC43A2 | ENSG00000167703\|ENSG00000278550 | 124935 | 23087 | Hs.160550 | 124935 |
| C5orf63 | ENSG00000164241 | 401207 | 40051 | Hs.49573 | 401207 |
| LOC1019278 | | | | | |
| DPP10 | ENSG00000175497 | 57628 | 20823 | | 57628 |
| LINC01267 | ENSG00000251576 | 101927565 | 50320 | Hs.306905 | 101927565 |
| INPP5A | ENSG00000068383 | 3632 | 6076 | Hs.523360 | 3632 |
| FRG2 | ENSG00000205097\|ENSG00000274972 | 448831 | 19136 | Hs.626907\|Hs.730594 | 448831 |

Fig. 1 (continued)

Table 1 (continued)

| | | | | | |
|---|---|---|---|---|---|
| CEP170B | ENSG00000099814 | 283638 | 20362 | Hs.533721 | 283638 |
| GALNT9 | ENSG00000182870 | 50614 | 4131 | Hs.658249 | 50614 |
| S100A13 | ENSG00000189171 | 6284 | 10490 | | 6284 |
| RPSAP58 | ENSG00000205246 | | 36809 | | |
| MIR7159 | ENSG00000276824 | 102466816 | 49978 | | 102466816 |
| GALNT2 | ENSG00000143641 | 2590 | 4124 | Hs.743964 | 2590 |
| NBPF25P | ENSG00000272150 | 101929780 | 45046 | | 101929780 |
| ABCC13 | ENSG00000243064 | 150000 | 16022 | Hs.366575 | 150000 |
| TSG1 | | | | | |
| MSX1 | ENSG00000163132 | 4487 | 7391 | Hs.424414 | 4487 |
| LOC401010 | | | | | |
| MMP10 | ENSG00000166670 | 4319 | 7156 | Hs.2258 | 4319 |
| PTCHD3 | ENSG00000182077\|ENSG00000276595 | 374308 | 24776 | Hs.631832 | 374308 |
| MEG9 | ENSG00000223403 | 100507257 | 43874 | Hs.301755 | 100507257 |
| EIF2AK4 | ENSG00000128829 | 440275 | 19687 | Hs.656673 | 440275 |
| UPP1 | ENSG00000183696 | 7378 | 12576 | Hs.488240 | 7378 |
| CCM2L | ENSG00000101331 | 140706 | 16153 | Hs.382151 | 140706 |
| AGR3 | ENSG00000173467 | 155465 | 24167 | | 155465 |
| ZNF385A | ENSG00000161642 | 25946 | 17521 | Hs.505653 | 25946 |
| LOC650226 | | | | | |
| TRPM3 | ENSG00000083067 | 80036 | 17992 | | 80036 |
| CTNNA2 | ENSG00000066032 | 1496 | 2510 | Hs.167368 | 1496 |
| FAM171A2 | ENSG00000161682 | 284069 | 30480 | | 284069 |
| PEG3 | ENSG00000198300 | 5178 | 8826 | Hs.731875 | 5178 |
| LOC338694 | | | | | |
| ARHGEF10 | ENSG00000104728\|ENSG00000274726\|LRG_234 | 9639 | 14103 | Hs.98594 | 9639 |
| COX4I2 | ENSG00000131055 | 84701 | 16232 | | 84701 |
| PLSCR1 | ENSG00000188313 | 5359 | 9092 | Hs.130759 | 5359 |
| CMTM2 | ENSG00000140932 | 146225 | 19173 | | 146225 |
| CNTN1 | ENSG00000018236 | 1272 | 2171 | Hs.143434 | 1272 |
| TUBGCP3 | ENSG00000126216 | 10426 | 18598 | Hs.224152 | 10426 |
| NAV1 | ENSG00000134369 | 89796 | 15989 | Hs.585374 | 89796 |
| SEPHS1 | ENSG00000086475 | 22929 | 19685 | Hs.124027 | 22929 |
| HTR2A | ENSG00000102468 | 3356 | 5293 | Hs.72630 | 3356 |
| NRXN1 | ENSG00000179915 | 9378 | 8008 | Hs.692121 | 9378 |
| GREB1 | ENSG00000196208 | 9687 | 24885 | Hs.467733 | 9687 |
| C1orf228 | ENSG00000198520 | 339541 | 34345 | Hs.173679\|Hs.734554 | 339541 |

Fig. 1 (continued)

Table 1 (continued)

| CASZ1 | ENSG00000130940 | 54897 | 26002 | Hs.439894\|Hs.685729\|Hs.743840 | 54897 |
|---|---|---|---|---|---|
| PRDM9 | ENSG00000164256 | 56979 | 13994 | Hs.283096 | 56979 |
| MAD1L1 | ENSG00000002822 | 8379 | 6762 | | 8379 |
| TNFRSF11A | ENSG00000141655\|LRG_194 | 8792 | 11908 | | 8792 |
| SERPINB8 | ENSG00000166401 | 5271 | 8952 | Hs.368077 | 5271 |
| DIP2C | ENSG00000151240 | 22982 | 29150 | Hs.432397 | 22982 |
| CYFIP1 | ENSG00000273749\|ENSG00000280618 | 23191 | 13759 | Hs.26704 | 23191 |
| CFAP74 | ENSG00000142609 | 85452 | 29368 | Hs.232092\|Hs.259619 | 85452 |
| DNAH17 | ENSG00000187775 | 8632 | 2946 | Hs.375975 | 8632 |
| CRISP2 | ENSG00000124490 | 7180 | 12024 | | 7180 |
| GLI2 | ENSG00000074047 | 2736 | 4318 | Hs.111867 | 2736 |

EPIGENETIC MARKERS FOR RESPIRATORY ALLERGY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This invention applies to the area of respiratory allergy diagnostics and prediction. In particular, it relates to epigenetic markers and their diagnostic and predictive value for respiratory allergy.

Description of the Related Art

Allergic diseases are increasing in frequency and severity. Respiratory allergy is the most common type of allergy, affecting 20-30% of the European population. According to the European Federation of Allergy and Airway Diseases Patients Association (EFA) 80 million (24.4%) adults living in Europe are allergic to inhalants or food allergens. Allergic diseases start in early childhood and only 60% have resolution by adulthood, indicating the chronic nature of allergic diseases. They pose a global challenge, because of the major societal and financial costs of caring for those with allergic diseases.

Although genetic predisposition is an important risk factor for the development of allergic diseases, the rise in prevalence happened within a too short time period to be explained by genetic changes in the population. There is convincing evidence that lifestyle factors including smoking, diet, and exposure to air pollution are major factors contributing to allergy risk. Growing evidence suggests that environmental exposures during fetal and early life enhance susceptibility to the development of allergic diseases later in life. The use of predictive biomarkers could contribute to the development of prevention strategies (including reduction of chemical exposures) to protect the offspring of exposed mothers-to-be. There is substantial evidence of perinatal biomarkers (e.g. folate levels, IgE-levels) predicting childhood allergy. Some work has been done to identify epigenetic markers with environmental exposure factors (e.g. Pascual et al. 2011, Epigenetics 6: 1131-1137; Perera et al. 2009, PLoS One 4, e4488).

There is need for predictive and diagnostic biomarkers for respiratory allergies. Ideally biomarkers should be available which can be detected in other biological samples than blood samples.

SUMMARY OF THE INVENTION

The present inventors have identified a number of markers in blood and saliva which are useful as diagnostic and prognostic markers for respiratory allergy. Moreover, it has been found that the genome-wide DNA methylation pattern both in healthy individuals and respiratory allergy patients is comparable in blood and saliva. Indeed, a disadvantage of the available biomarkers for respiratory allergy is that they require blood sampling, which is often cumbersome in children. Saliva may be a good alternative for testing molecular biomarkers as it can be easily collected from children at all ages and it contains a broad range of diagnostically relevant molecules, such as DNA, microRNA and antibodies. The feasibility of assessing DNA methylation patterns in saliva is subject to debate. Thompson et al. (2013, Behav Genet 43:168-176) tested the feasibility of assessing DNA methylation patterns in saliva and observed that patterns were consistent with those in blood. This study was however confined to healthy volunteers. Godderis et al. (2009, Biomed Res Intl) conclude based on their findings that saliva DNA cannot be considered as a surrogate for blood DNA to study epigenetic endpoints.

The present invention is in particular captured by any one or any combination of one or more of the below numbered aspects and embodiments (i) to (xv) wherein.

(i) The application provides methods for diagnosing or predicting the development of a respiratory allergy in a patient, said method comprising assaying a test sample from the patient for DNA hypermethylation or hypomethylation of at least one gene region, wherein hypermethylation or hypomethylation of said gene region in said test sample indicates or predicts a respiratory allergy in said patient. Preferably, said at least one gene region is selected from the group consisting of the regions of genes GLI2, CRISP2, DNAH17, CFAP74, CYFIP1, DIP2C, SERPINB8, TNFRSF11A, MAD1L1, PRDM9, CASZ1, C1orf228, GREB1, NRXN1, HTR2A, SEPHS1, NAV1, TUBGCP3, CNTN1, CMTM2, PLSCR1, COX4I2, ARHGEF10, LOC338694, PEG3, FAM171A2, CTNNA2, TRPM3, LOC650226, ZNF385A, AGR3, CCM2L, UPP1, EIF2AK4, MEG9, PTCHD3, MMP10, LOC401010, MSX1, TSG1, ABCC13, NBPF25P, GALNT2, MIR7159, RPSAP58, S100A13, GALNT9, CEP170B, FRG2, INPP5A, LINC01267, DPP10, LOC101927815, C5orf63, SLC43A2, CUX1, SMAD3, PSG4, PM20D1, GATA3-AS1, LOC441666, LINC00839, LINC01475, CYP2E1, GRAMD1B, DDX11, ONECUT1, SLC12A4, HSF5, PARD6G, NRBP1, NECAB3, OSBPL2, GADL1, CKMT2, NKAPL, TAPBP, PON1, LEP, TM9SF2, HLA-DRA; HLA-DRB1, PRDM8, PDCD1, PCNT, RUNX3, LRCOL1, VWA3A, RTP5, LINC00676, EGFL7, MAST3, PRDM1, ABAT, ATF3, CELF6, NOSIP, CYP26C1, DEAF1, STOX2, GHRL, TMEM80, MYT1L, ACBD4, BLOC1S4, and RPTOR, as defined in Tables 3, 4 or to 5.

(ii) In particular embodiments, the methods as envisaged herein comprise assaying a test sample from the patient for DNA hyper- or hypomethylation of at least the GLI2 region as defined in Tables 3, 4 or 5 herein, and, optionally, for DNA hyper- or hypomethylation of at least one gene region selected from the group consisting of the regions of genes CRISP2, DNAH17, CFAP74, CYFIP1, DIP2C, SERPINB8, TNFRSF11A, MAD1L1, PRDM9, CASZ1, C1orf228, GREB1, NRXN1, HTR2A, SEPHS1, NAV1, TUBGCP3, CNTN1, CMTM2, PLSCR1, COX4I2, ARHGEF10, LOC338694, PEG3, FAM171A2, CTNNA2, TRPM3, LOC650226, ZNF385A, AGR3, CCM2L, UPP1, EIF2AK4, MEG9, PTCHD3, MMP10, LOC401010, MSX1, TSG1, ABCC13, NBPF25P, GALNT2, MIR7159, RPSAP58, S100A13, GALNT9, CEP170B, FRG2, INPP5A, LINC01267, DPP10, LOC101927815, C5orf63, SLC43A2, CUX1, SMAD3, PSG4, PM20D1, GATA3-AS1, LOC441666, LINC00839, LINC01475, CYP2E1, GRAMD1B, DDX11, ONECUT1, SLC12A4, HSF5, PARD6G, NRBP1, NECAB3, OSBPL2, GADL1, CKMT2, NKAPL, TAPBP, PON1, LEP, TM9SF2, HLA-DRA; HLA-DRB1, PRDM8, PDCD1, PCNT, RUNX3, LRCOL1, VWA3A, RTP5, LINC00676, EGFL7, MAST3, PRDM1, ABAT, ATF3, CELF6, NOSIP, CYP26C1, DEAF1, STOX2, GHRL, TMEM80, MYT1L, ACBD4, BLOC1S4, and RPTOR, as defined in Tables 3, 4 or 5.

(iii) In more particular embodiments, the test sample is assayed for hypermethylation of at least the GLI2 gene region as defined in Table 3 or 4, and/or hypomethylation of at least the TM9SF2 gene region as defined in Table 3 or 4, and wherein the test sample is a saliva sample, a peripheral blood sample or a cord blood sample.

(iv) In particular embodiments of the methods envisaged herein, the methods are for diagnosing a respiratory allergy in a patient wherein the test sample is assayed for hypermethylation of the region of at least one gene, particularly at least the GLI2 gene region as defined in Table3, selected from the group comprising: GLI2, CRISP2, DNAH17, CFAP74, CYFIP1, DIP2C, SERPINB8, TNFRSF11A, MAD1L1, PRDM9, CASZ1, C1orf228, GREB1, NRXN1, HTR2A, SEPHS1, NAV1, TUBGCP3, CNTN1, CMTM2, PLSCR1, COX4I2, ARHGEF10, LOC338694, PEG3, FAM171A2, CTNNA2, TRPM3, LOC650226, ZNF385A, AGR3, CCM2L, UPP1, EIF2AK4, MEG9, PTCHD3, MMP10, LOC401010, MSX1, TSG1, ABCC13, NBPF25P, GALNT2, MIR7159, RPSAP58, S100A13, GALNT9, CEP170B, FRG2, INPP5A, LINC01267, DPP10, LOC101927815, C5orf63, SLC43A2, CUX1, SMAD3, PSG4 and PM20D1, as defined in Table 3, and/or hypomethylation of the region of at least one gene selected from the group comprising: TM9SF2, HLA-DRB1, PRDM8, PDCD1, PCNT, RUNX3, LRCOL1, VWA3A, RTP5, LINC00676, EGFL7, MAST3, PRDM1, ABAT, ATF3, CELF6, NOSIP, CYP26C1, DEAF1, STOX2, GHRL, TMEM80, and MYT1L, as defined in Table 3, and wherein the test sample is a peripheral blood sample.

(v) In particular embodiments of the methods envisaged herein, the test sample is assayed for hypermethylation of at least the GLI2 gene region as defined in Table 3, and/or hypomethylation of at least the TM9SF2 gene region or the HLA-DRA region as defined in Table 3.

(vi) In further particular embodiments of the methods provided herein, said methods are methods for diagnosing a respiratory allergy in a patient wherein the test sample is assayed for hypermethylation of at least the GLI2 gene region as defined in Table 4 and/or for hypomethylation of at least the TM9SF2 gene region, the HLA-DRA region, the ACBD4 gene region or the BLOC1S4 gene region as defined in Table 4, and wherein the test sample is a saliva sample.

(vii) A further particular embodiments of the methods provided herein are methods for predicting a respiratory allergy in a patient, wherein the test sample is assayed for hypermethylation of at least one gene region, preferably at least the GLI2 gene region as defined in Table 5, selected from the group consisting of: the gene regions of GLI2, UPP1, LOC101927815, C5orf63, GATA3-AS1, LOC441666, LINC00839, LINC01475, CYP2E1, GRAMD1B, DDX11, ONECUT1, SLC12A4, HSF5, PARD6G, NRBP1, NECAB3, OSBPL2, GADL1, CKMT2, NKAPL, TAPBP, PON1 and LEP, as defined in Table 5, and/or hypomethylation of at least the TM9SF2 or RPTOR gene region as defined in Table 5, and wherein the test sample is a cord blood sample.

(viii) The application further provides methods for diagnosing or predicting the development of a respiratory allergy in a patient wherein the test sample is a cord blood or blood sample and wherein the sample is assayed for hypermethylation of the GLI2 gene region as defined in Table 3 for a blood sample or Table 5 for a cord blood sample, and, optionally, hypermethylation of at least one gene region selected from the group consisting of: the gene regions of UPP1, LOC101927815 and C5orf63, as defined in Table 3 for a blood sample or Table 5 for a cord blood sample, and/or hypomethylation of at least the TM9SF2 gene region as defined in in Table 3 for a blood sample or Table 5 for a cord blood sample.

(ix) In particular embodiments of the methods envisaged herein, the methylation status of at least one, preferably between 2 and 20 CpG dinucleotides located in said gene regions, is determined.

(x) In further particular embodiments of the methods envisaged herein the methylation frequency of at least one, preferably between 2 and 20 CpG dinucleotides located in at least one gene region, is determined.

(xi) The application provides methods for diagnosing or predicting the development of a respiratory allergy in a patient as detailed hereinabove, wherein the methylation status of said at least one gene region, is determined by one or more techniques selected from the group comprising: nucleic acid amplification, polymerase chain reaction (PCR), methylation specific PCR (MCP), methylated-CpG island recovery assay (MIRA), combined bisulfite-restriction analysis (COBRA), bisulfite pyrosequencing, single-strand conformation polymorphism (SSCP) analysis, restriction analysis, microarray analysis, or bead-chip technology.

(xii) The application further provides computer programs, which, when run on a computer linked to a device for determining the methylation status of DNA present in a sample, is configured to selectively determine the methylation status of one or more gene regions as identified in Tables 3, 4 or 5 herein, preferably is configured to selectively determine the methylation status of the GLI2 gene region as identified in Tables 3, 4 or 5 herein, and, optionally the methylation status of one or more gene regions as identified in Tables 3, 4 or 5 herein.

(xiii) In accordance with the above, the application relates to the use of the methylation status of at least one gene region selected from the group consisting of: the gene regions of GLI2, CRISP2, DNAH17, CFAP74, CYFIP1, DIP2C, SERPINB8, TNFRSF11A, MAD1L1, PRDM9, CASZ1, C1orf228, GREB1, NRXN1, HTR2A, SEPHS1, NAV1, TUBGCP3, CNTN1, CMTM2, PLSCR1, COX4I2, ARHGEF10, LOC338694, PEG3, FAM171A2, CTNNA2, TRPM3, LOC650226, ZNF385A, AGR3, CCM2L, UPP1, EIF2AK4, MEG9, PTCHD3, MMP10, LOC401010, MSX1, TSG1, ABCC13, NBPF25P, GALNT2, MIR7159, RPSAP58, S100A13, GALNT9, CEP170B, FRG2, INPP5A, LINC01267, DPP10, LOC101927815, C5orf63, SLC43A2, CUX1, SMAD3, PSG4, PM20D1, GATA3-AS1, LOC441666, LINC00839, LINC01475, CYP2E1, GRAMD1B, DDX11, ONECUT1, SLC12A4, HSF5, PARD6G, NRBP1, NECAB3, OSBPL2, GADL1, CKMT2, NKAPL, TAPBP, PON1, LEP, TM9SF2, HLA-DRA; HLA-DRB1, PRDM8, PDCD1, PCNT, RUNX3, LRCOL1, VWA3A, RTP5, LINC00676, EGFL7, MAST3, PRDM1, ABAT, ATF3, CELF6, NOSIP, CYP26C1, DEAF1, STOX2, GHRL, TMEM80, MYT1L, ACBD4, BLOC1S4, and RPTOR, as defined in Tables 3, 4 or 5, as a biomarker for respiratory allergy in a patient, preferably the methylation status of at least the GLI2 gene region as defined in Tables 3, 4 or 5.

(xiv) A further aspect of the invention provides a diagnostic kit for assessing a respiratory allergy comprising a discrete set of probes which selectively allow the determination of the methylation status of one or more gene regions as identified in Tables 3, 4 or 5, preferably allow the determination of the methylation status of at least the GLI2 gene region as defined in Tables 3, 4 or 5, and, optionally, the methylation status of one or more other gene regions as identified in Tables 3, 4 or 5.

(xv) A further aspect of the invention relates to the use of saliva in an in vitro method for the diagnosis or prediction of a respiratory allergy based on methylation markers, in particular based on the methylation status of the GLI2 gene region as defined in Table 4.

BRIEF DESCRIPTION OF THE DRAWINGS

In the following detailed description of the invention and examples, reference is made to the accompanying drawings that form a part here of, and in which are shown by way of illustration only of specific embodiments in which the invention may be practiced. It is to be understood that other embodiments may be utilised and structural or logical changes may be made without departing from the scope of the present invention.

FIG. 1: Table 1 provides the standard nomenclature, as well as the accession number for the genomic reference sequence of the marker genes envisaged for use in the methods provided herein, derived all from Homo sapiens. Source: National Center for Biotechnology Information (NCBI). The listed accession numbers may be found in the publicly available gene database at http://www.ncbi.nlm.nih.gov.

DETAILED DESCRIPTION OF THE PREFERRED EMBODIMENT

Figure 2:
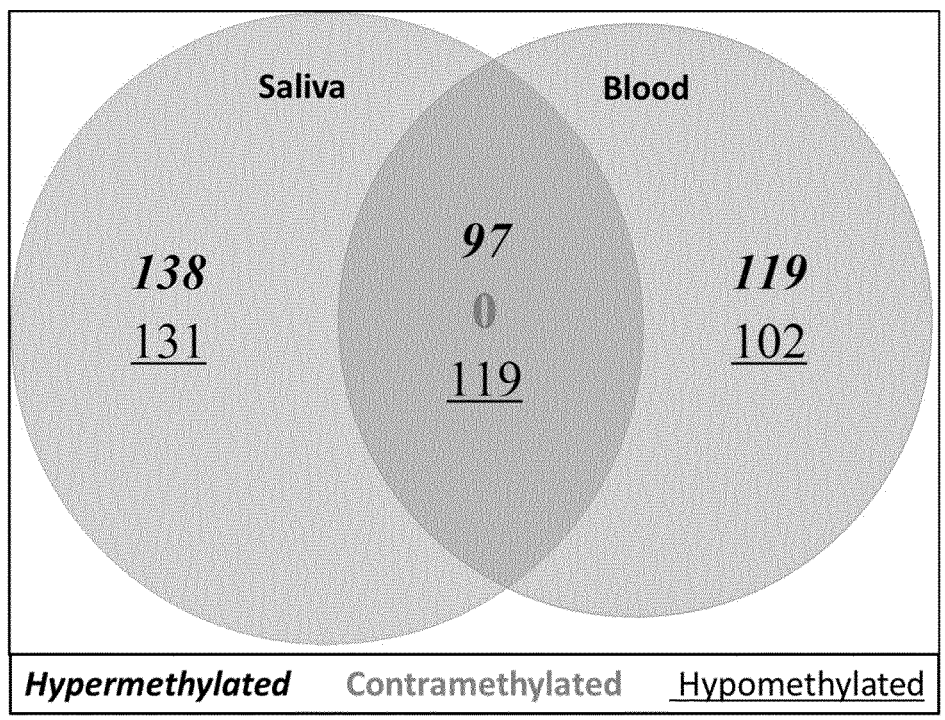
FIG. 2: Identification of differentially methylated probes (DMPs) between respiratory allergy cases and healthy controls in blood and saliva samples. 216 probes were in common in blood and saliva. The common probes showed the same polarity of methylation levels.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The term "regulatory region" or the equivalent "regulatory sequence," in respect of a specific gene, refers to a region of the non-coding nucleotide sequences within that gene that are necessary or sufficient to provide for the regulated expression of the coding region of said gene. Thus, the term "regulatory region" includes promoter sequences, regulatory protein binding sites, upstream activator sequences, and the like. Specific nucleotides within a regulatory region may serve multiple functions. For example, a specific nucleotide may be part of a promoter and participate in the binding of a transcriptional activator protein.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. It is understood by those skilled in the art that different promoters may direct the expression of a gene in different tissues or cell types, or at different stages of development, or in response to different environmental conditions. Typically, a "promoter" region extends between approximately 1 Kb, 500 bp or 150 to 300 bp upstream from the transcription start site.

The term "CpG island" is a G:C-rich region of genomic DNA containing a greater number of CpG dinucleotides relative to total genomic DNA, as defined in the art. In many genes, the CpG islands begin just upstream of a promoter and extend downstream into the transcribed region. The islands can also surround the 5' region of the coding region of the gene as well as the 3' region of the coding region. CpG islands can be found in multiple regions of a gene like upstream of coding regions in a regulatory region including a promoter region; within the coding regions (e.g., exons); downstream of coding regions in, for example, enhancer regions; or within introns. All of these regions can be assessed to determine their methylation status.

As used herein, a "methylated nucleic acid molecule" refers to a nucleic acid molecule that contains one or more methylated nucleotides. A gene, a region thereof, or a CpG island thereof as described herein comprising at least one methylated nucleotide, preferably a methylated CpG dinucleotide, can be considered methylated (i.e. the methylation state of the gene, gene region, or CpG island is methylated). A gene, a region thereof, or a CpG island thereof as described herein that does not comprise any methylated nucleotides can be considered unmethylated.

As used herein, a "methylated nucleotide" or a "methylated nucleotide base" refers to the presence of a methyl moiety on a nucleotide base, where the methyl moiety is not present in a recognized typical nucleotide base. Cytosine does not contain a methyl moiety on its pyrimidine ring, however 5-methylcytosine contains a methyl moiety at position 5 of its pyrimidine ring. In this respect, cytosine is not a methylated nucleotide and 5-methylcytosine is a methylated nucleotide.

As used herein, a "methylated CpG dinucleotide" refers to the presence of a methyl moiety on the cytosine nucleotide of the CpG dinucleotide, i.e. the presence of 5-methylcytosine in a CpG dinucleotide.

As used herein, a "methylation profile" or "methylation state" or "methylation status" correlated with respiratory allergy refers to a specific methylation state of a gene, a gene region, a CpG island or a CpG dinucleotide that is present or absent more frequently in subjects with respiratory allergy or having a risk of developing a respiratory allergy than otherwise occur in a larger population of individuals (e.g., a population of all individuals).

As used herein "CpG dinucleotide" refers to a nucleic acid region where a cytosine nucleotide occurs next to a guanine nucleotide in the linear sequence of bases along its length.

As used herein, a "methylation site" is a nucleotide within a nucleic acid that is susceptible to methylation either by natural occurring events in vivo or by an event instituted to methylate the nucleotide in vitro.

The term "methylation status" or "methylation state" or "methylation profile," when used herein to describe the state of methylation of a gene, a gene region, or a CpG island as described herein refers to the characteristics of said gene, said gene region or said CpG island at a particular locus relevant to methylation, e.g. at one or more particular CpG dinucleotides. Such characteristics include, but are not limited to, whether any of the cytosine (C) residues within this gene, gene region or CpG island are methylated, location of methylated C residue(s), ratio or percentage of methylated C at any particular stretch of residues, and allelic differences in methylation due to, e.g., difference in the origin of the alleles.

By "aberrant methylation" is meant altered methylation of cytosine (C) residues of one or more CpG dinucleotides in a gene, gene region or CpG island as described herein. Such altered methylation is measured in comparison to the same regions of the gene, gene region or CpG island in a control sample. Two forms of aberrant methylation are possible: hypermethylation and hypomethylation.

The term "hypermethylation," when used in reference to a gene, a gene region, or a CpG island as described herein means that the characteristics relevant to methylation as described above are found in a relative abundance. For example, a nucleic acid, in particular a gene, a gene region or a CpG island as described herein may be "hypermethylated," which refers to the nucleic acid, in particular the gene, the gene region or the CpG island, having a greater number of methylatable nucleotides or CpG dinucleotides that are methylated relative to a control or reference. A nucleic acid, in particular a gene, a gene region or a CpG island as described herein, may be "hypomethylated," which refers to the nucleic acid, in particular the gene, the gene region or the CpG island, having a smaller number of methylatable nucleotides or CpG dinucleotides that are methylated relative to a control or reference.

The term "allergy" is defined herein as an immune-mediated inflammatory response to common environmental allergens that are otherwise harmless. With "respiratory allergy" is specifically meant herein an allergy that affects the respiratory tract. Respiratory allergies most likely appear in the form of allergic rhinitis and asthma, but other forms of respiratory allergy are also intended herein. "Allergic rhinitis", also known as hay fever, is caused by allergic reactions of the mucous membranes in the nose and airway to allergens in the air. Symptoms of allergic rhinitis often include itchy nose, throat and eyes and excessive sneezing. Stuffy or runny nose often follow. "Asthma" occurs in the lungs. It is characterized by the development of airway hyper-reactivity, breathlessness, wheezing on exhale, dry cough and a feeling of tightness in the chest. Repeated allergen exposure can sustain the inflammatory immune response in the airways, resulting in a remodeling of the airways, commonly known as chronic asthma.

As used herein, the terms "diagnosis", "diagnostic", "diagnosing", and the like refer to establishing and concluding that a subject is affected by a recited disease or disorder, in particular a respiratory allergy. Diagnosis may also refer to monitoring the treatment and recovery of a subject affected by the recited disease or disorder. The diagnosis may be based on the examination of symptoms associated with a recited disease or disorder (i.e. clinical or medical diagnosis). Alternatively or in addition, the diagnosis may be made through, e.g., detecting biomarkers indicative for the recited disease or disorder and/or imaging techniques.

The term "marker" is synonym to "biomarker" or "biological marker" in the present invention. A "biomarker," as used herein, refers to an organic biomolecule which is differentially present in a sample taken from a subject of one phenotypic status (e.g., having a disease) as compared with another phenotypic status (e.g., not having the disease). It is differentially present between different phenotypic statuses if the mean methylation of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Based on the invention detailed herein, differential methylation of the biomarkers in a test sample from a patient relative to a control sample makes it possible to diagnose or predict a respiratory allergy. The term "preclinical marker" refers to a biomarker as defined above, which has not yet been validated in a clinical trial.

As used herein, "methylation ratio" refers to the number of instances in which a molecule or locus is methylated relative to the number of instances the molecule or locus is unmethylated. Methylation ratio can be established regarding a population of individuals or in respect of a sample from a single individual. For example, a CpG dinucleotide having a methylation ratio of 50% is methylated in 50% of instances and unmethylated in 50% of instances. Such a ratio can be used, for example, to describe the degree to which a molecule or locus is methylated in a population of individuals. Thus, when methylation in a first population or pool of nucleic acid molecules is different from methylation in a second population or pool of nucleic acid molecules, the methylation ratio of the first population or pool will be different from the methylation ratio of the second population or pool. Alternatively such a ratio can be used to describe the degree to which a nucleotide locus or nucleic acid region is methylated in a single individual. For example, such a ratio can be used to describe the degree to which a gene, a gene region, or a CpG island of a group of cells from a test sample, are methylated or unmethylated at a nucleotide locus or methylation site, in particular a CpG dinucleotide.

As used herein, the terms "prediction", "predictive", "predicting" and the like refer to establishing and concluding that a subject is prone to develop or at risk of developing a recited disease or disorder, in particular a respiratory allergy.

As used herein, a "patient" refers to an animal subject. Among animal subjects are mammals, including primates, such as humans. Preferably, the patient is a human subject. The term "patient" may be used interchangeably with "subject" or "individual". In the context of the present invention, when considering prenatal or neonatal prediction of the susceptibility to a respiratory allergy, the "patient" as used herein is the child or offspring to which the prediction applies, while it will be understood that in principle the cord blood originates in part from the mother of the patient.

The term "test sample" generally refers to biological material obtained from a patient, and may be e.g. a tissue sample or a body fluid (e.g. blood, lymph fluid, serum, plasma, saliva, cord blood). Any suitable test sample in which hyper- or hypomethylation of the relevant gene(s) (region) can be determined is included within the scope of the invention.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Disclosed herein are biomarkers for use in a method for diagnosing or predicting a respiratory allergy in a patient. Indeed, it has been found that epigenetic markers can be used to diagnose and/or predict the development of respiratory allergy in a patient. More particularly, the application identifies a number of gene regions, the methylation status of which can be correlated with the presence or predicted development of a respiratory allergy in said patient. The ability to use epigenetic markers to diagnose respiratory allergy in a sample of a patient has not been previously disclosed, let alone the use of these specific genes or gene regions in this context.

More particularly, the application provides for one or more genes selected from the group consisting of GLI2, CRISP2, DNAH17, CFAP74, CYFIP1, DIP2C, SERPINB8, TNFRSF11A, MAD1L1, PRDM9, CASZ1, C1orf228, GREB1, NRXN1, HTR2A, SEPHS1, NAV1, TUBGCP3, CNTN1, CMTM2, PLSCR1, COX4I2, ARHGEF10, LOC338694, PEG3, FAM171A2, CTNNA2, TRPM3, LOC650226, ZNF385A, AGR3, CCM2L, UPP1, EIF2AK4, MEG9, PTCHD3, MMP10, LOC401010, MSX1, TSG1, ABCC13, NBPF25P, GALNT2, MIR7159, RPSAP58, S100A13, GALNT9, CEP170B, FRG2, INPP5A, LINC01267, DPP10, LOC1019278, C5orf63, SLC43A2, CUX1, SMAD3, PSG4, PM20D1, GATA3-AS1, LOC441666, LINC00839, LINC01475, CYP2E1, GRAMD1B, DDX11, ONECUT1, SLC12A4, HSF5, PARD6G, NRBP1, NECAB3, OSBPL2, GADL1, CKMT2, NKAPL, TAPBP, PON1, LEP, TM9SF2, HLA-DRA; HLA-DRB1, PRDM8, PDCD1, PCNT, RUNX3, LRCOL1, VWA3A, RTP5, LINC00676, EGFL7, MAST3, PRDM1, ABAT, ATF3, CELF6, NOSIP, CYP26C1, DEAF1, STOX2, GHRL, TMEM80, MYT1L, ACBD4, BLOC1S4, and RPTOR as listed in Table 1 in FIG. 1, or a gene region thereof as identified in Tables 3, 4 and 5 for use as a biomarker for diagnosing or predicting a respiratory allergy in a patient or the offspring thereof.

Table 1 provided in FIG. 1 provides the standard nomenclature, as well as the accession number for the genomic reference sequence of the marker genes envisaged for use in the methods provided herein, derived all from Homo sapiens. Source: National Center for Biotechnology Information (NCBI). The listed accession numbers may be found in the publicly available gene database at http://www.ncbi.nlm.nih.gov. The genomic molecules presented herein are not limited to the particular sequences referred to above, but also comprise variants thereof.

Additionally, the application provides in general methods for diagnosing or predicting a respiratory allergy in a patient or an offspring thereof based on the methylation states of at least one gene or a region of said in a sample comprising DNA of said patient. More particularly, the genes of which regions have been identified for which the methylation status is correlated with respiratory allergy are provided in Table 1 in FIG. 1. In particular embodiments, the methods comprise determining the methylation status of the region of said at least one gene as defined in Tables 3, 4 and 5 herein.

It has further been determined that for some genes or gene regions, the development and/or presence of respiratory allergy is correlated with hypomethylation of said gene or gene region, while for other genes hypermethylation is indicative of the presence or development of respiratory allergy in the patient. Accordingly, in embodiments of the methods of the present invention, the sample is assayed for hypermethylation and/or hypomethylation of one or more genes or gene regions provided herein.

Typically, the methods of the present invention are carried out on a test sample in vitro. Accordingly, the application provides in vitro methods for diagnosing or predicting the development of a respiratory allergy in a patient or an offspring of said patient, the method comprising assaying a test sample from the patient for DNA hypermethylation or hypomethylation of at least one gene region, wherein hypermethylation of said at least one gene region and/or hypomethylation of said at least one gene region in said test sample indicates or predicts a respiratory allergy in said patient.

More particularly, the methods as envisaged herein comprise assaying a test sample from a patient for hypermethylation of at least the GLI2 gene region as defined in Tables 3, 4 or 5, and optionally, for hypermethylation of at least one gene or a region of a gene selected from the group comprising or consisting of: CRISP2, DNAH17, CFAP74, CYFIP1, DIP2C, SERPINB8, TNFRSF11A, MAD1L1, PRDM9, CASZ1, C1orf228, GREB1, NRXN1, HTR2A, SEPHS1, NAV1, TUBGCP3, CNTN1, CMTM2, PLSCR1, COX4I2, ARHGEF10, LOC338694, PEG3, FAM171A2, CTNNA2, TRPM3, LOC650226, ZNF385A, AGR3, CCM2L, UPP1, EIF2AK4, MEG9, PTCHD3, MMP10, LOC401010, MSX1, TSG1, ABCC13, NBPF25P, GALNT2, MIR7159, RPSAP58, S100A13, GALNT9, CEP170B, FRG2, INPP5A, LINC01267, DPP10, LOC101927815, C5orf63, SLC43A2, CUX1, SMAD3, PSG4, PM20D1, GATA3-AS1, LOC441666, LINC00839, LINC01475, CYP2E1, GRAMD1B, DDX11, ONECUT1, SLC12A4, HSF5, PARD6G, NRBP1, NECAB3, OSBPL2, GADL1, CKMT2, NKAPL, TAPBP, PON1 and LEP, and/or hypomethylation of at least one gene or a region of a gene selected from the group comprising or consisting of: TM9SF2, HLA-DRA; HLA-DRB1, PRDM8, PDCD1, PCNT, RUNX3, LRCOL1, VWA3A, RTP5, LINC00676, EGFL7, MAST3, PRDM1, ABAT, ATF3, CELF6, NOSIP, CYP26C1, DEAF1, STOX2, GHRL, TMEM80, MYT1L, ACBD4, BLOC1S4, and RPTOR, preferably TM9SF2 and/or HLA-DRA, more preferably TM9SF2, wherein hypermethylation of said GLI2 and, optionally said at least one gene or gene region and/or hypomethylation of said at least one gene or gene region in said test sample indicates or predicts a respiratory allergy. In particular embodiments, the gene regions indicative of the presence or development of respiratory allergy are those listed in Tables 3 to 5 herein.

In particular embodiments of the methods disclosed herein hypermethylation of said at least one gene region and/or hypomethylation of said at least one gene region as corresponding to the status provided in Tables 3 to 5, in said test sample is indicative of the presence of or the predisposition of said patient (or where applicable, its offspring) to develop a respiratory allergy. In particular, said at least one gene region comprises the GLI2 gene region as listed in Tables 3 to 5 herein.

In particular embodiments, biomarkers as disclosed herein are used for the diagnosing respiratory allergy in a patient. Typically the patient is a patient showing one or more clinical symptoms of respiratory allergy, such as one or more symptoms of rhinitis or asthma as described herein below. However, in particular embodiments, the patient does not show any particular clinical symptoms of respiratory allergy. Most particularly, these methods are performed on a blood sample of a patient.

The inventors have further found that epigenetic markers can be used for the diagnosis of respiratory allergy in a saliva sample. This is in contrast to previous reports wherein it was considered that saliva samples would not be suitable for the detection of epigenetic markers. Moreover, it has been found that the salivary inflammatory profile does not reflect the inflammatory profile of either the upper or lower airways, questioning the diagnostic and predictive use of salivary samples. However, it has been established by the present inventors that overall methylation patterns in blood and saliva are comparable for respiratory allergy (only 11% difference), which suggests the usefulness of saliva as alternative for blood, in particular the mononuclear cell fraction of blood, for analyzing epigenetic markers in the diagnosis or prediction of respiratory allergy. This is of particular interest for the diagnosis of patients when taking a blood sample is less desirable such as for children, the elderly or diseased patients.

More particularly it has been found that the methylation status of particular genes or gene regions thereof as can be determined in saliva is correlated with the diagnosis of respiratory allergy, i.e. GLI2, TM9SF2, HLA-DRA, ACBD4 and BLOC1S4. Accordingly, provided herein are methods for diagnosing a respiratory allergy in a patient comprising determining the methylation status of one or more of GLI2, TM9SF2, HLA-DRA, ACBD4 and BLOC1S4 or a region thereof as determined in Table 4 herein in a saliva sample of said patient. Most particularly, the invention provides methods for diagnosing a respiratory allergy in a patient comprising determining the hypermethylation of at least the GLI2 gene region as defined in Table 4 and, optionally, determining the hypomethylation of at least the TM9SF2 gene region, the HLA-DRA gene region, the ACBD4 gene region and/or the BLOC1S4 gene region, more particularly hypomethylation of one or both of the TM9SF2 gene region and the HLA-DRA gene region, most particularly hypomethylation of the TM9SF2 gene region as defined in Table 4, and wherein the test sample is a saliva.

The inventors have moreover analysed the correlation of DNA methylation in cord blood with the development of respiratory allergy as diagnosed later in life. It has been found that the methylation of particular genes or gene regions in cord blood taken upon birth is indicative of the development of respiratory allergy of the then born child (referred to herein as "the patient") later in life. Accordingly, in particular embodiments, the application provides methods for predicting a respiratory allergy in an offspring of a patient, said method comprising assaying a sample from the cord blood of said patient for hypermethylation or hypomethylation of one or more of said genes.

More particularly, the inventors have found that the methylation status of the following genes or a region thereof as present in cord blood is correlated with the development of respiratory allergy of the patient later in life: GLI2, UPP1, LOC101927815 and C5orf63, GATA3-AS1, LOC441666, LINC00839, LINC01475, CYP2E1, GRAMD1B, DDX11, ONECUT1, SLC12A4, HSF5, PARD6G, NRBP1, NECAB3, OSBPL2, GADL1, CKMT2, NKAPL, TAPBP, PON1 and LEP, TM9SF2 and RPTOR. More particularly it has been found that for particular genes hypermethylation of the gene or a region thereof is associated with the development of respiratory allergy later in life and for other genes hypomethylation of the gene or a region thereof is associated with the development of respiratory allergy later in life. Accordingly, more particularly, methods are provided for predicting a respiratory allergy in a patient, wherein the blood cord sample taken at birth of said patient is assayed for hypermethylation of at least one gene selected from the group consisting of: GLI2, UPP1, LOC101927815, C5orf63, GATA3-AS1, LOC441666, LINC00839, LINC01475, CYP2E1, GRAMD1B, DDX11, ONECUT1, SLC12A4, HSF5, PARD6G, NRBP1, NECAB3, OSBPL2, GADL1, CKMT2, NKAPL, TAPBP, PON1 and LEP, or a region of these genes as defined in Table 5, and/or hypomethylation of at least the TM9SF2 or RPTOR gene or a region thereof as defined in Table 5. Most particularly, the invention provides methods for diagnosing a respiratory allergy in a patient comprising determining the hypermethylation of at least the GLI2 gene region as defined in Table 5 and, optionally, determining the hypermethylation of at least one gene selected from the group consisting of: UPP1, LOC101927815, C5orf63, GATA3-AS1, LOC441666, LINC00839, LINC01475, CYP2E1, GRAMD1B, DDX11, ONECUT1, SLC12A4, HSF5, PARD6G, NRBP1, NECAB3, OSBPL2, GADL1, CKMT2, NKAPL, TAPBP, PON1 and LEP, or a region of these genes as defined in Table 5, and/or hypomethylation of at least the TM9SF2 or RPTOR gene or a region thereof as defined in Table 5. In particular embodiments of these methods, the sample is a cord blood sample. It is however envisaged that such prognosis is equally possible based on blood obtained during early childhood.

More particularly, it has been found that some of these genes or regions thereof are also hypermethylated or hypomethylated in blood samples of patients diagnosed with respiratory allergy. Based thereon these are preferred targets for predicting respiratory allergy at any stage until the clinical diagnosis can be performed and/or for confirming clinical diagnosis. Accordingly, in particular embodiments, methods are provided for predicting a respiratory allergy in a patient, said methods comprising assaying a sample from the patient for the methylation status of a gene selected from GLI2, UPP1, LOC101927815, 5orf63 or TM9SF2 or a gene region thereof as defined in Tables 3 or 5 herein, in a blood sample of said patient. Most particularly, when the sample is blood, the region of these genes as identified in Table 3 is assayed. Most particularly, methods are provided for predicting a respiratory allergy in a patient, said methods comprising assaying a sample from the patient for hypermethylation of the GLI2 gene region as defined in Table 3 or 5, and, optionally, for hypermathylation of at least one gene region selected from the group consisting of: the gene regions of UPP1, LOC101927815 and C5orf63, as defined in Table 3 or 5, and/or hypomethylation of at least the TM9SF2 gene region as defined in Table 3 or 5. In particular embodiments, the samples are of a patient which has not yet been clinically diagnosed with respiratory allergy. In further particular embodiments, the method is used on a patient which does not yet show clinical signs or not all signs of respiratory allergy. In further embodiments, the method is used to confirm a clinical diagnosed of respiratory allergy in a patient.

The inventors have further found that a number of these predictive markers are also detectable in saliva. Accordingly, not only are these biomarkers of particular interest for use in predicting the development of respiratory allergy in the methods described above, but moreover these markers can be used as predictive markers based on saliva samples. Accordingly; in further particular embodiments, the application provides methods for predicting a respiratory allergy in a patient said method comprising assaying a test sample comprising determining the methylation status of GLI2 and, optionally, TM9SF2 or a gene region thereof as defined in Table 4 herein in a sample of said patient. In further particular embodiments, the method comprises assaying a test sample from the patient for hypermethylation of at least GLI2 or a region thereof as defined in Table 4, and, optionally, hypomethylation of at least TM9SF2 or a region thereof as defined in Table 4, wherein hypermethylation of said at least one gene and, optionally, hypomethylation of said at least one gene or region thereof as defined in Table 4 in said test sample predicts a respiratory allergy. In further particular embodiments, the methods are performed on a saliva sample.

The invention further relates to the use of the methylation status of one or more genes described above as a marker or preclinical marker of respiratory allergy in a patient.

The specific procedures envisaged in the methods described herein are detailed below.

A test sample can be obtained from a subject in any way typically used in clinical settings for obtaining a sample comprising the required cell(s) or biological molecule such as nucleic acid, including RNA, genomic DNA, mitochondrial DNA, and protein-associated nucleic acids, and/or protein. The nature of the sample can be dependent on the nature of the analysis performed, the time point of the analysis and the availability of the samples.

In the methods provided herein, the test sample may be peripheral blood, in particular the mononuclear cell fraction of peripheral blood. Methods for collecting peripheral blood are well known in the art.

In particular embodiments, the test sample is cord blood, in particular the mononuclear cell fraction of cord blood. Cord blood refers to a sample of blood collected from the umbilical cord when a baby is born. Typically, right after birth the umbilical cord is clamped and cut. Another clamp is placed 10 to 15 cm away from the first. The section between the clamps is cut and a blood sample is collected into a specimen tube.

In particular embodiments of the methods provided herein, the test sample is saliva. Methods for obtaining saliva are known in the art and include dry or wet procedures or simple spitting into a vial. Dry procedures involve introducing a collection device such as a cytobrush or a buccal swab into the mouth where tissue is scraped from the gum and cheek surfaces. Wet procedures include swishing liquids (such as mouthwash) in the mouth and spitting them into a collecting vessel. Examples of commercially available kits for collecting a saliva sample include but are not limited to the Oragene® DNA kit from DNA Genotek and SalivaGene collector from Stratec Molecular.

The samples may be treated in one or more purification steps in order to increase the purity of the desired cells or biological molecules in the sample, or they may be examined without any purification steps. For example, blood samples, including peripheral blood samples and cord blood samples, may be processed for isolating the mononuclear cell fraction by density gradient centrifugation. Any nucleic acid specimen in purified or non-purified form obtained from such test sample can be utilized in the methods of the present invention.

In particular embodiments of the methods of the present invention, genomic DNA is isolated from the test sample from the patient for methylation analysis. Genomic DNA may be isolated by any means standard in the art, including the use of commercially available kits. Briefly, wherein the DNA is encapsulated by a cellular membrane the test sample must be disrupted and lysed by enzymatic, chemical or mechanical means. The DNA solution may then be cleared of proteins and other contaminants e.g. by digestion with proteinase K. The DNA is then recovered from the solution. This may be carried out by means of a variety of methods including salting out, organic extraction or binding of the DNA to a solid phase support. The choice of method will be affected by several factors including time, expense and required quantity of DNA. Wherein the DNA is not enclosed in a membrane (e.g. circulating DNA from a blood sample) methods standard in the art for the isolation and/or purification of DNA may be employed. Such methods include the use of a protein degenerating reagent e.g. chaotropic salt e.g. guanidine hydrochloride or urea; or a detergent e.g. sodium dodecyl sulphate (SDS), cyanogen bromide. Alternative methods include but are not limited to ethanol precipitation or propanol precipitation, vacuum concentration amongst others by means of a centrifuge. The person skilled in the art may also make use of devices such as filter devices e.g.

ultrafiltration, silica surfaces or membranes, magnetic particles, polystyrene particles, polystyrene surfaces, positively charged surfaces, and positively charged membranes, charged membranes, charged surfaces, charged switch membranes, charged switched surfaces. Once the nucleic acids have been extracted, the genomic double stranded DNA is used in the methylation analysis.

In particular embodiments, the methods comprise determining the methylation status of one or more genes or gene regions listed in Table 1 more particularly the gene regions thereof listed herein in Tables 3 to 5, most particularly, the GLI2 gene region as listed in Tables 3 to 5.

Determining the methylation status of one or more gene, or determining the methylation status of a region of said genes as defined in Tables 3 to 5, or, most particularly determining the methylation status of the GLI2 gene region as defined in Tables 3 to 5 may comprise determining the methylation status of one or more CpG islands of said at least one gene or gene region as defined in Tables 3 to 5. Accordingly, in particular embodiments of the methods of the present invention, the test sample is assayed for hypermethylation and/or hypomethylation one or more CpG islands of said at least one gene or gene region as defined in Tables 3 to 5, particularly the GLI2 gene region. In particular embodiments, the methods comprise determining the methylation status of at least one or more, such as two, three, four, five, six, seven, eight or more, such as up to 20 CpG dinucleotides in said at least one gene, gene region, or CpG island. In particular embodiments, the methylation status of all of the CpG dinucleotides in said at least one gene, gene region, or CpG island as defined in Tables 3 to 5 is determined. The methylated CpG dinucleotides may be located in a coding region, such as the 5' and 3' untranslated regions, or an exon, as well as in a non-coding region, including a regulatory region such as the promoter region, of the gene. The methylated CpG dinucleotides may be located inside or outside a CpG island.

In embodiments, the detection of the methylation status of one or more of the genes envisaged herein in Table 1 or the region of one or more of said gene as defined in Tables 3 to 5, particularly the GLI2 gene region, or the CpG island of one or more of said gene as defined in Tables 3 to 5, comprises:
a. determining the methylation status of said at least one gene, gene region, or CpG island in a test sample from the patient; and
b. comparing the methylation status of said at least one gene, gene region or CpG island obtained in step a) to the methylation status of the same said at least one gene, gene region or CpG island in a control sample;
wherein an increase in methylation status indicates that said at least one gene, gene region or CpG island is hypermethylated and wherein a decrease in methylation status indicates that said at least one gene, gene region or CpG island is hypomethylated.

The control sample is preferably a test sample from a non-allergic patient.

The actual level of increase or decrease in methylation status in the test sample from the patient is less relevant in the context of the present invention and can be between 0.25 and 10%.

The methylation status of a gene, a gene region, a CpG island as described herein may be determined by any technique for detecting methylated nucleic acid molecules. These techniques are based on any one or more of the classic techniques of hybridization, amplification, sequencing, electrophoresis, chromatography, and mass spectrometry and combinations thereof, amongst others, and include, for example, but without limitation, the polymerase chain reaction (PCR), methylated CpG island recovery assay (MIRA), combined bisulfite-restriction analysis (COBRA), MALDI-TOFF, MassARRAY, MethyLight, Quantitative analysis of methylated alleles (QAMA), Enzymatic regional methylation assay (ERMA), HeavyMethyl, QBSUPT, MS-SNuPE, MethylQuant, Quantitative PCR sequencing, (bisulfite) pyrosequencing, single-strand conformation polymorphism (SSCP) analysis, restriction analysis, bead-chip technology, ligase chain reaction, microarray analysis, and oligonucleotide-based microarray, or next generation sequencing methods such as, but not limited to Massively parallel signature sequencing (MPSS), Polony sequencing, 454 pyrosequencing, Illumina (Solexa) sequencing, SOLiD sequencing, Ion Torrent semiconductor sequencing, DNA nanoball sequencing, Heliscope single molecule sequencing and Single molecule real time (SMRT) sequencing amongst others. Some of these are described more in detail below.

Methylation specific PCR (U.S. Pat. Nos. 5,786,146, 6,017,704, 6,200,756) allows the distinction between modified and unmodified DNA by hybridizing oligonucleotide primers which specifically bind to one form or the other of the DNA. After hybridization, an amplification reaction can be performed and amplification products assayed. The presence of an amplification product indicates that a sample hybridized to the primer. The specificity of the primer indicates whether the DNA had been modified or not, which in turn indicates whether the DNA had been methylated or not. For example, bisulfite ions modify non-methylated cytosine bases, changing them to uracil bases. Uracil bases hybridize to adenine bases under hybridization conditions. Thus an oligonucleotide primer which comprises adenine bases in place of guanine bases would hybridize to the bisulfite-modified DNA, whereas an oligonucleotide primer containing the guanine bases would hybridize to the non-modified (methylated) cytosine residues in the DNA. Amplification using a DNA polymerase and a second primer yield amplification products that can be readily observed. The amplification products can be optionally hybridized to specific oligonucleotide probes which may also be specific for certain products. Alternatively, oligonucleotide probes can be used which will hybridize to amplification products from both modified and non-modified DNA.

With real-time methylation specific PCR, the methylation profile of the genes, gene regions or CpG islands of interest can be assessed by determining the amplification level of said genes, gene regions or CpG islands based on amplification-mediated displacement or on binding of one or more probes whose binding sites are located within the amplicon. In general, real-time quantitative methylation specific PCR is based on the continuous monitoring of a progressive fluorogenic PCR by an optical system. Such PCR systems usually use two amplification primers and an additional amplicon-specific, fluorogenic hybridization probe that specifically binds to a site within the amplicon. The probe can include one or more fluorescence label moieties. For example, the probe can be labeled with two fluorescent dyes: 1) a 6-carboxy-fluorescein (FAM), located at the 5'-end, which serves as reporter, and 2) a 6-carboxy-tetramethyl-rhodamine (TAMRA), located at the 3'-end, which serves as a quencher. When amplification occurs, the 5'-3' exonuclease activity of the Taq DNA polymerase cleaves the reporter from the probe during the extension phase, thus releasing it from the quencher. The resulting increase in fluorescence emission of the reporter dye is monitored during the PCR process and represents the number of DNA fragments generated. This process is known as Taqman. Other systems to monitor real-time PCR involve the use of hairpin primers (Amplifluor), hairpin probes (Molecular Beacons), FRET probe pairs (Lightcycler), primers incorporating a hairpin probe (Scorpion), Plexor™ system, primers incorporating complementary sequences of DNAzymes that cleave a reporter substrate included in the reaction mixture (DzyNA) or fluorescent dyes (SYBR Green etc.)

Methylation-dependent sequence variation at CpG dinucleotide motifs offers different approaches to PCR primer design. In one approach, oligonucleotide primers are designed to specifically bind methylated primer-binding sites, and a probe is designed to anneal specifically within the amplicon during extension. Such primers typically comprise CpG dinucleotides which get affected by DNA methylation. In another approach, oligonucleotide primers are designed to bind either methylated or unmethylated primer-binding sites, and the probe is designed to anneal specifically to methylated probe binding sites. In yet another approach, both oligonucleotide primers and probes are designed to specifically bind methylated binding sites. In either approach, when there is a sufficient region of complementarity, e.g., 12, 15, 18, or 20 nucleotides, between the target and the primer, the primer may also contain additional nucleotide residues that do not interfere with hybridization but may be useful for other manipulations. Exemplary of such other residues may be sites for restriction endonuclease cleavage, for ligand binding, or for factor binding or linkers or repeats.

Another way to distinguish between modified and non-modified DNA employs oligonucleotide probes which may also be specific for certain products. Such probes can be hybridized directly to modified DNA or to amplification products of modified DNA. Oligonucleotide probes can be labeled using any detection system known in the art. These include but are not limited to fluorescent moieties, radio-isotope labeled moieties, bioluminescent moieties, luminescent moieties, chemiluminescent moieties, enzymes, substrates, receptors, or ligands. The oligonucleotide probes may be bound to a support. The support can be any suitable support such as plastic materials, (fluorescent) beads, magnetic beads, synthetic or natural membranes, latex beads, polystyrene, column supports, glass beads or slides, nanotubes, fibres or other organic or inorganic supports. The binding processes are well-known in the art and generally comprise cross-linking, covalently binding or physically adsorbing the oligonucleotide to the support. A support may also contain a plurality of oligonucleotide probes arrayed on the support. Such array may comprise multiple copies of the same oligonucleotide probe so as to capture the same target gene (region) on the array or may comprise a plurality of different oligonucleotide probes targeting different genes (regions) so as to capture a plurality of target genes (regions) on the array. An exemplary method for detecting the methylation status of a nucleic acid based on the use of oligonucleotide probes is the use of Infinium® BeadChip sold by Illumine Inc. San Diego (US), which makes use of a bead chip.

MethyLight relies on methylation-specific priming combined with methylation-specific fluorescent probing, resulting in a highly methylation-specific detection technology.

Another approach for assessing the methylation status of a gene, a gene region, a CpG island uses methylation-sensitive restriction endonucleases to detect methylated CpG dinucleotide motifs. Such endonucleases may either preferentially cleave methylated recognition sites relative to non-methylated recognition sites, or preferentially cleave non-methylated relative to methylated recognition sites. Examples of the former are Acc III, Ban I, BstN I, Msp I, and Xma I. Examples of the latter are Acc II, Ava I, BssH II, BstU I, Hpa II, and Not I. Yet another approach is the combined bisulfite-restriction analysis (COBRA assay) in which PCR products obtained from bisulfite-treated DNA are further analyzed by using restriction enzymes that recognize sequences containing 5'CG, such as TaqI (5'TCGA) or BstUI (5'CGCG), such that methylated and unmethylated DNA can be distinguished.

Following digestion of sample DNA with either methylation-sensitive or methylation-insensitive restriction enzymes (for ex. MspI and HpaII), the DNA can be analyzed by methods such as Southern Blotting and PCR. Southern blot analysis involves electrophoretic separation of the resulting DNA fragments and hybridization with a labeled probe adjacent to the CpG of interest. If the hybridization signal from the methylation-sensitive and methylation-insensitive digested DNA samples results in different size bands, than the site of interest was methylated. In contrast, PCR analysis involves amplification across the CpG of interest. The expected band will only be observed in the methylation-sensitive digested sample if the site of interest is methylated. The PCR assay requires much lower amounts of DNA for each site of interest (for ex: 1-10 ng), but necessitates the design and testing of specific primer pairs for every site of interest.

Still another way for the identification of methylated CpG dinucleotides utilizes the ability of the MBD domain of the MeCP2 protein to selectively bind to methylated DNA sequences (Cross et al, 1994; Shiraishi et al, 1999). Restriction endonuclease digested genomic DNA is loaded onto expressed His-tagged methyl-CpG binding domain that is immobilized onto a solid matrix and used for preparative column chromatography to isolate highly methylated DNA sequences.

Yet an alternative for analysing the methylation status of a gene, gene region, CpG island or CpG dinucleotide is the EpiTYPER®. The EpiTYPER® assay uses DNA that has been treated with a reagent that selectively modifies an unmethylated cytosine residue but which is incapable of modifying a methylated cytosine residue. During a PCR selected DNA regions are amplified using specific primers, followed by an in vitro transcription into RNA and a base-specific cleavage by endoribonucleases. The cleavage products are analyzed by the Matrix assisted Laser Desorption/Ionization Time Of Flight Mass Spectrometry (MALDI-TOF MS). Methylated and unmethylated fragments differ in mass as result of the differential cleavage and the analytical software will quantify the methylation percentage.

Alternatively, the HELP assay can be used, which is based on the differential ability of restriction enzymes to recognize and cleave methylated and unmethylated CpG DNA sites.

Furthermore, ChIP-on-chip assays, based on the ability of commercially prepared antibodies to bind to DNA methylation-associated proteins like MCP2, can be used to determine the methylation status. Also restriction landmark genomic scanning, also based upon differential recognition of methylated and unmethylated CpG sites by restriction enzymes can be used. Methylated DNA immunoprecipitation (MeDIP), analogous to chromatin immunoprecipitation, can be used to isolate methylated DNA fragments for input into DNA detection methods such as DNA microarrays (MeDIP-chip) or DNA sequencing (MeDIP-seq). The unmethylated DNA is not precipitated. Alternatively, molecular break light assay for DNA adenine methyltransferase activity can be used. This is an assay that uses the specificity of the restriction enzyme DpnI for fully methylated (adenine methylation) GATC sites in an oligonucleotide labeled with a fluorophore and quencher. The adenine methyltransferase methylates the oligonucleotide making it a substrate for DpnI. Cutting of the oligonucleotide by DpnI gives rise to a fluorescence increase. Further, methylated-CpG island recovery assay (MIRA) can be used.

Typically, for determining the methylation status of a gene, a gene region, a CpG island or a CpG dinucleotide, genomic DNA or a fragment thereof, is treated with a reagent that selectively modifies an unmethylated cytosine residue but which is incapable of modifying a methylated cytosine residue; and the resulting product is detected. Examples of reagents for selective modification of unmethylated cytosine residues include hydrazine and bisulfite ions. Hydrazine-modified DNA, or a portion thereof, can be treated with piperidine to cleave it. Bisulfite ion-treated DNA, or a portion thereof, can be treated with alkali. The resulting products can be detected directly, or after a further reaction that creates products, which are easily distinguishable. For example, the products resulting from the treatment with a reagent that selectively modifies an unmethylated cytosine residue but which is incapable of modifying methylated cytosine residue, may be detected by amplification with at least one primer that hybridizes to a sequence comprising a modified non-methylated CpG dinucleotide motif, i.e. UpG or TpG, but not to a sequence comprising an unmodified methylated CpG dinucleotide motif, thereby forming amplification products. Conversely, the resulting products may be detected by amplification with at least one primer that hybridizes to a sequence comprising an unmodified methylated CpG dinucleotide motif but not to a sequence comprising a modified non-methylated CpG, i.e. UpG or TpG, dinucleotide motif, thereby forming amplification products. In addition, the amplification products under investigation may be detected using (a) a first oligonucleotide probe which hybridizes to a sequence comprising a modified non-methylated CpG dinucleotide motif, i.e. UpG or TpG, but not to a sequence comprising an unmodified methylated CpG dinucleotide motif, (b) a second oligonucleotide probe that hybridizes to a sequence comprising an unmodified methylated CpG dinucleotide motif but not to a sequence comprising a modified non-methylated CpG dinucleotide motif, i.e. UpG or TpG, or (c) both said first and second oligonucleotide probes.

Accordingly, in embodiments of the methods described herein, determining the methylation status of a gene, a gene region, a CpG island or a CpG dinucleotide as described herein, particularly the GLI2 gene or gene region, comprises:
 a) isolating genomic DNA from a test sample from the patient;
 b) contacting the genomic DNA obtained in step a) with at least one reagent that selectively modifies an unmethylated cytosine residue but which is incapable of modifying a methylated cytosine residue;
 c) detecting the modified DNA obtained in step b) with a technique as described above.

The application further provides tools such as kits for diagnosing or predicting the development of respiratory allergy in a patient, the kits comprising probes for determining the methylation status of at least one gene provided in Table 1 or the region of said at least one gene as provided in Tables 3 to 5, preferably the methylation status of at least the GLI2 gene region as provided in Tables 3 to 5. More particularly, the application provides kits for determining either hypermethyation or hypomethylation of these genes or gene regions as described herein.

More particularly provided in the kits envisaged herein are probes which allow the determination of the methylation status of one or more genes selected from GLI2, CRISP2, DNAH17, CFAP74, CYFIP1, DIP2C, SERPINB8, TNFRSF11A, MAD1L1, PRDM9, CASZ1, C1orf228, GREB1, NRXN1, HTR2A, SEPHS1, NAV1, TUBGCP3, CNTN1, CMTM2, PLSCR1, COX4I2, ARHGEF10, LOC338694, PEG3, FAM171A2, CTNNA2, TRPM3, LOC650226, ZNF385A, AGR3, CCM2L, UPP1, EIF2AK4, MEG9, PTCHD3, MMP10, LOC401010, MSX1, TSG1, ABCC13, NBPF25P, GALNT2, MIR7159, RPSAP58, S100A13, GALNT9, CEP170B, FRG2, INPP5A, LINC01267, DPP10, LOC1019278, C5orf63, SLC43A2, CUX1, SMAD3, PSG4, PM20D1, GATA3-AS1, LOC441666, LINC00839, LINC01475, CYP2E1, GRAMD1B, DDX11, ONECUT1, SLC12A4, HSF5, PARD6G, NRBP1, NECAB3, OSBPL2, GADL1, CKMT2, NKAPL, TAPBP, PON1 and LEP, TM9SF2, HLA-DRA; HLA-DRB1, PRDM8, PDCD1, PCNT, RUNX3, LRCOL1, VWA3A, RTP5, LINC00676, EGFL7, MAST3, PRDM1, ABAT, ATF3, CELF6, NOSIP, CYP26C1, DEAF1, STOX2, GHRL, TMEM80, MYT1L, ACBD4, BLOC1S4, and RPTOR as listed in Table 1, or a gene region thereof as identified in Table 3 to 5. More specifically, the kits allow the specific determination of the methylation status of one or more of these genes, particularly including the GLI2 gene region as provided in Tables 3 to 5. Most particularly in specific embodiments, the kits comprise probes which allow determining the methylation frequency of at least the GLI2 gene of Table 1 or a gene region thereof as identified in Table 3 to 5 and optionally a limited number of control genes or gene regions, but do not enable a genome wide determination of methylation frequency.

More particularly, the application provides kits for the diagnosis or prediction of respiratory allergy on a saliva sample. These kits comprise one or more reagents suitable for determining the methylation status of one or more genes selected from the group consisting of GLI2, TM9SF2, HLA-DRA, ACBD4 and BLOC1S4, particularly of at least the GLI2 gene or a region thereof. Accordingly, provided herein are kits for diagnosing a respiratory allergy in a patient comprising probes for determining the methylation status of one or more of GLI2, TM9SF2, HLA-DRA, ACBD4 and BLOC1S4 or a region thereof as determined in Table 4 herein in a saliva sample of a patient. Most particularly, the kits comprise probes for determining the hypermethylation or hypomethylation status of these genes as determined in Table 4. Most particularly the kits will comprise probes for determining the methylation status of at least the GLI2 gene or a region thereof, and, optionally, one or more genes selected from the group comprising or consisting of TM9SF2 and/or HLA-DRA or a region thereof as defined in Table 4, more preferably TM9SF2 or a region thereof as defined in Table 4. The kits may further comprise one or more reagents suitable for determining methylation status of DNA in a saliva sample, such as but not limited reagents for DNA extraction from saliva as described above. In particular embodiments the kit comprises a tool for saliva collection ("saliva collector") from a patient as described above.

In further embodiments, the application provides kits for the prediction of the development of a respiratory allergy in a patient in blood, more particularly in cord blood. More particularly these may comprise tools such as probes for determining the methylation status of one or more genes selected from the group consisting of GLI2, UPP1, LOC101927815, C5orf63, GATA3-AS1, LOC441666, LINC00839, LINC01475, CYP2E1, GRAMD1B, DDX11, ONECUT1, SLC12A4, HSF5, PARD6G, NRBP1, NECAB3, OSBPL2, GADL1, CKMT2, NKAPL, TAPBP, PON1, LEP, TM9SF2 and RPTOR, most particularly of at least the GLI2 gene or a region thereof as defined in Table 5. Most particularly such kits may comprise tools such as probes suitable for determining the hypermethylation or hypomethylation of one or more of these genes or regions thereof as identified in Table 5. Most particularly these kits may involve tools for extracting DNA from cord blood.

The kits as envisaged herein typically comprise tools for the specific detection of the genes or gene regions of which the methylation status is to be assessed. In particular embodiments the kits comprise tools such as primers which identify only those genes or gene regions of which the methylation status is to be assessed, particularly of at least the GLI2 gene or a region thereof. In particular embodiments, the kits comprise an array in which the arrangement of the probes is such that the probes detecting the genes or gene regions of which the methylation frequency is to be assessed in the context of diagnosing or predicting a respiratory allergy, are marked in some way, either by spatial organization or by a visual identification.

The application further provides computer programs for carrying out the methods described herein, wherein said programs, when carried out on a computer allow the skilled person to diagnose or predict respiratory allergy based on the methylation status of the specific genes listed herein. In particular embodiments, said methods ensure selecting the genes or gene regions listed herein, determining the methylation status based on the outcome of an assay as described herein and providing an output as to the methylation status of the specific set of genes or gene regions as envisaged herein.

The application further envisages the potential use of the biomarkers disclosed herein in as vivo diagnostic or predictive markers. Indeed, it is expected that in particular circumstances in vivo diagnosis or prediction (such as prenatal determination) of a respiratory allergy can be of interest. A particular aspect of the invention thus provides one or more gene regions selected from the gene regions of GLI2, CRISP2, DNAH17, CFAP74, CYFIP1, DIP2C, SERPINB8, TNFRSF11A, MAD1L1, PRDM9, CASZ1, C1orf228, GREB1, NRXN1, HTR2A, SEPHS1, NAV1, TUBGCP3, CNTN1, CMTM2, PLSCR1, COX4I2, ARHGEF10, LOC338694, PEG3, FAM171A2, CTNNA2, TRPM3, LOC650226, ZNF385A, AGR3, CCM2L, UPP1, EIF2AK4, MEG9, PTCHD3, MMP10, LOC401010, MSX1, TSG1, ABCC13, NBPF25P, GALNT2, MIR7159, RPSAP58, S100A13, GALNT9, CEP170B, FRG2, INPP5A, LINC01267, DPP10, LOC101927815, C5orf63, SLC43A2, CUX1, SMAD3, PSG4, PM20D1, GATA3-AS1, LOC441666, LINC00839, LINC01475, CYP2E1, GRAMD1B, DDX11, ONECUT1, SLC12A4, HSF5, PARD6G, NRBP1, NECAB3, OSBPL2, GADL1, CKMT2, NKAPL, TAPBP, PON1, LEP, TM9SF2, HLA-DRA; HLA-DRB1, PRDM8, PDCD1, PCNT, RUNX3, LRCOL1, VWA3A, RTP5, LINC00676, EGFL7, MAST3, PRDM1, ABAT, ATF3, CELF6, NOSIP, CYP26C1, DEAF1, STOX2, GHRL, TMEM80, MYT1L, ACBD4, BLOC1S4, and RPTOR, as defined in Tables 3 to 5, most particularly of at least the GLI2 gene or a region thereof for use as an in vivo diagnostic or prognostic marker.

The following non-limiting examples help to illustrate the principles of the invention.

EXAMPLES

Example 1: Comparability of Saliva and Blood DNA Methylation Patterns in Respiratory Allergy Cases Materials and Methods
Study Design and Population Ten adult volunteers, 5 females and 5 males, were recruited for this pilot study. 5 persons suffered from respiratory allergy (RA) and 5 individuals never showed any symptoms of RA. All volunteers completed a survey (based on the International Study of Asthma and Allergies in Children (ISAAC) (Asher et al., 1995)), including questions on: (1) occurrence and severity of RA symptoms, (2) clinical management and medical treatment and (3) family history of allergies. The study was approved by the ethical committee of the University Hospital in Antwerp (file number 13/2/22, Belgian registration number B300201316329). Before sample collection, all volunteers signed a consent form.

Sample Collection and Preparation

Blood samples (10 mL) were collected in an EDTA tube (BD Vacutainer®, BD, Plymouth, UK) from each participant and stored at room temperature (<2h) until further processing. The collected blood was processed as follows: in a first step plasma was removed by centrifugation at 800×g for 5 min. Next, Lymphoprep™ (Axis-Shield, Oslo, Norway) was used for the isolation of a pure mononuclear cell (MNC) suspension. The suspension was then divided into two aliquots originating from 5 mL of the whole blood and spun down (10 min, 300×g at 4° C.) to create MNC pellets, which were stored at −80° C. until DNA extraction.

Matched saliva samples (2 mL) were collected using an Oragene DNA OG-500 self-collection kit, (DNA Genotek, Ottawa, Canada). The saliva samples were kept at room temperature until DNA extraction.

DNA Extraction

DNA extraction from the MNC pellets was completed with the Gentra Puregene Blood Kit (Qiagen, Hilden, Germany) according to the Buffy coat protocol (no red blood cell content) with an optional RNAse digestion step. DNA from the saliva samples was extracted using the Oragene PrepIT kit (DNA Genotek, Ottawa, Canada) according to the manufacturer's protocol. Final DNA concentrations were measured using the NanoDrop spectrophotometer, and confirmed using the Qubit® 2.0 Fluorometer.

DNA Methylation Profiling

Samples (500 ng of genomic DNA) were bisulfite treated using the EZ DNA Methylation™ Kit (Zymo Research, Irvine, USA) according to the manufacturer's protocol. DNA samples were incubated overnight in a PCR machine under following conditions: (95° C. for 30 sec, 50° C. for 60 mins) for 16 cycles and then the samples were hold at 4° C. The bisulfite treated DNA was eluted in 12 µl of elution buffer and concentrations were checked on the NanoDrop.

DNA methylation was analysed by Infinium HumanMethylation450 BeadChip Array (Illumina, San Diego, Calif., USA). This technology interrogates the methylation status of more than 480 000 CpGs, thereby allowing for an almost whole-genome analysis of DNA methylation and covering 99% of the RefSeq genes. These CpG sites are not only found in CpG islands, but also in CpG shores and shelves (respectively within 2 kb and >2 kb from the CpG islands), 3'- and 5' UTRs and gene bodies (Dedeurwaerder et al., 2011). 4 µl of bisulfite-converted DNA (~150 ng) was used for the whole genome amplification reaction. DNA methylation analysis was carried out according to the standard Infinium HD Assay Methylation Protocol Guide (Part #15019519, Illumina). The BeadChip images were captured using the Illumina iScan. The raw methylation intensities for each probe were represented as β-values. This methylation level is the ratio of the methylated probe to the overall intensity (a sum of the methylated and unmethylated probe intensities) and is defined as:

$$\beta = \frac{\text{Max}(M, 0)}{\text{Max}(M, 0) + \text{Max}(U, 0) + 100}$$

where Max (M,0) and Max (U,0) are the intensities measured by the methylated and unmethylated probe. The β-values range from 0 to 1, where 0 means that the CpG site was completely unmethylated and 1 means that the CpG site was fully methylated (Bibikova and Fan, 2009).

Data Processing and Statistical Analysis

Raw array data were extracted from GenomeStudio Methylation module software without background correction and normalization. Processing, quality control, filtering and normalization of data were performed in the R-based software package, RnBeads (http://rnbeads.mpi-inf.mpg.de/). Probes were filtered out according to the following criteria: A) probes with a missing value (NA) in at least one sample or having a detection p-value ≥0.01, B) probes measuring methylation in a non-CpG context, C) probes on sex chromosomes, and D) probes containing more than two single-nucleotide polymorphisms or minor allele frequency (MAF) >0.01. Methylation values of all remaining probes were normalized using the Beta Mixture Quantile dilation (BMIQ). Normalized β-values were converted to M-values ($M=\log_2(\beta/(1-\beta))$) and differential methylation was estimated using the R-based package Limma (v3.20.9). Resulting P-values were corrected for multiple hypothesis testing using the Benjamini-Hochberg procedure ($P_{Adj}$).

Results

To test the usefulness of saliva as an alternative for blood DNA methylation patterns, a genome-wide Infinium HumanMethylation450 BeadChip array was performed on DNA derived from saliva and MNC from each of the participants (N=10).

Following quality filtering 451,731 individual cg-probes scattered across the genome were within array normalized (BMIQ normalization) and used to evaluate patterns of DNA methylation between the groups. About 4% of all studied CpG loci showed difference in DNA methylation of 20% or more between blood and saliva ($P_{Adj}$<0.001) (Table 2), of which 29% were hyper- and 71% were hypomethylated in saliva DNA;

Table 2: Distribution of Differentially Methylated Probes (Expressed as Delta Beta) Between Blood and Saliva.

| Histogram breaks (ΔBeta Blood vs Saliva) | Histogram counts (No of cg probes) (based on ΔBeta) | Histogram counts (No of cg probes) (based on ΔBeta and P <0.001) | Histogram counts (No of cg probes) (based on ΔBeta and $P_{Adj}$ <0.001) |
|---|---|---|---|
| −0.8 to −0.7 | 2 | 2 | 2 |
| −0.7 to −0.6 | 16 | 16 | 16 |
| −0.6 to −0.5 | 110 | 110 | 110 |
| −0.5 to −0.4 | 457 | 457 | 457 |
| −0.4 to −0.3 | 1133 | 1132 | 1132 |
| −0.3 to −0.2 | 3451 | 3451 | 3451 |
| −0.2 to −0.1 | 12848 | 12728 | 12531 |
| −0.1 to 0 | 167141 | 27347 | 20169 |
| 0.0 to 0.1 | 230232 | 64315 | 51403 |
| 0.1 to 0.2 | 23522 | 23355 | 23106 |
| 0.2 to 0.3 | 6491 | 6488 | 6485 |
| 0.3 to 0.4 | 3099 | 3099 | 3099 |
| 0.4 to 0.5 | 1725 | 1725 | 1725 |
| 0.5 to 0.6 | 973 | 973 | 973 |
| 0.6 to 0.7 | 406 | 406 | 406 |
| 0.7 to 0.8 | 109 | 109 | 109 |
| 0.8 to 0.9 | 16 | 16 | 16 |
| total no of probes: | 451731 | 145729 | 125190 |
| (% of total no. of probes) | 100.000 | 32.260 | 27.713 |
| No. of probes Δβ > \|0.1\| | 54358 | 54067 | 53618 |
| (% of total no. of probes) | 12.033 | 11.969 | 11.869 |
| No. of probes Δβ > \|0.2\| | 17988 | 17984 | 17981 |
| (% of total no. of probes) | 3.982 | 3.981 | 3.980 |
| No. of probes Δβ > \|0.3\| | 8046 | 8045 | 8045 |
| (% of total no. of probes) | 1.781 | 1.781 | 1.781 |

These data show that overall methylation patterns in blood and saliva are comparable, which suggests the usefulness of saliva as alternative for blood, in particular the mononuclear cell fraction of blood, for analyzing epigenetic markers.

Further, 437 probes in blood and 485 probes in saliva were identified which showed significant (P<0.05) DNA methylation alterations of at least 10% difference between RA cases and healthy controls (FIG. 2). Remarkably, for the differentially methylated probes (DMPs) that met the above-mentioned criteria, 216 DMPs (corresponding to 97 unique genes) between allergic individuals and healthy controls were common between blood and saliva. More importantly, the polarity of methylation alterations in these CG probes was consistent (97 probes were hyper- and 119 probes were hypomethylated in RA cases as compared to the healthy individuals) in blood as well as in saliva, making them potential candidates for biomarker discovery in saliva. Furthermore, to establish whether respiratory allergy-specific variation in methylation in blood was reflected in saliva DNA, Spearman correlations between the two matrices were computed for all significantly altered CG loci. Both hyper- (ρ=0.78, P<0.001) and hypomethylated probes (ρ=0.74, P<0.001) revealed strong and significant correlations between blood and saliva (FIG. 3A-B).

These data show that the patterns of respiratory allergy-specific DNA methylation alterations are highly conserved between blood and saliva.

Example 2: Discovery of Diagnostic Epigenetic Markers in Saliva

Materials and Methods

Study Design and Population

The data gathered herein originate from an ongoing birth cohort in Flanders (Flanders Environment and Health Surveys FLEHS1) using the Infinium® HumanMethylation450k platform.

A case-control study design nested in a large-scale human biomonitoring surveillance programme (Flanders Environment and Health Survey FLEHS1) was used. FLESH1 was initiated in 2004 by the Flemish Centre of Expertise on Environment and Health (financed by the Flemish Government). 1200 Mother/child pairs were recruited and cord blood samples were collected At 10 years of age, 65.2% of the children developed some form of allergy, of which 13.8% respiratory allergy. A follow-up study at the age of 11 years was conducted in a subcohort (n=99) of FLEHS1, from whom lymphocyte pellets from cord blood samples were available. This subcohort was asked to confirm allergy status using a brief questionnaire, and blood and saliva samples were collected and analysed. Respiratory allergy (RA) cases were identified via questionnaires as "doctor's diagnosed allergy" at age 10 and each case was matched with controls; matching criteria included gender, living area, social economic status. The case-control study included 20 RA cases and 20 healthy controls.

Sample collection and preparation, DNA extraction, bisulfite treatment and DNA methylation profiling using Infinium HumanMethylation450 BeadChip Array (Illumina, San Diego, Calif., USA) were performed as described in Example 1.

Data Processing and Statistical Analysis

Raw array data were extracted from GenomeStudio Methylation module software without background correction and normalization. Processing, quality control, filtering and normalization of data were performed in the R-based software package, IMA- and Limma pipeline. Probes were filtered out according to the following criteria: A) probes with a missing value (NA) in at least one sample or having a detection P-value ≥0.01, B) probes measuring methylation in a non-CpG context, C) probes on sex chromosomes, and D) probes containing more than two single-nucleotide polymorphisms or minor allele frequency (MAF) >0.01. Methylation values of all remaining probes were normalized using the Subset-quantile Within Array Normalization (SWAN). Resulting P-values were corrected for multiple hypothesis testing using the Benjamini-Hochberg procedure ($P_{Adj}$). Parameters such as age and IgE values were included as covariates. Tools like Comb-p (Pedersen, B. S. et al. 2012) were used to identify differentially methylated regions (DMR) between RA cases and controls.

Results

When comparing the genome-wide methylation pattern, using $P_{Adj}$<0.001; |Δβ|>|0.2| as selection criteria, 16575 probes (~3.5%) could be identified which showed significant differences in DNA methylation patterns in saliva DNA as compared to blood DNA of the total study population, (RA cases and healthy controls combined), confirming the results obtained in Example 1 that the overall DNA methylation pattern is comparable in blood and saliva.

Figure 3:
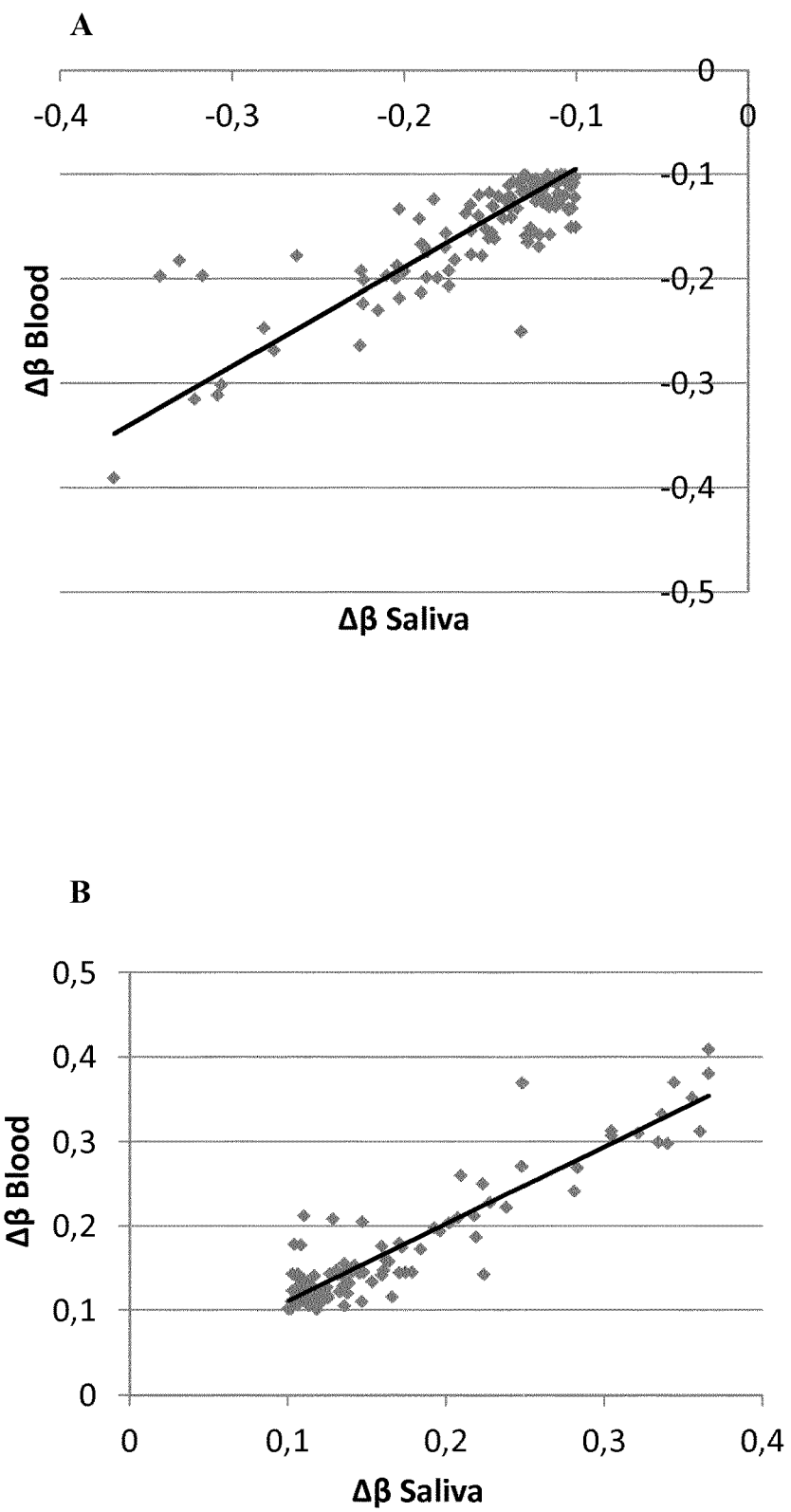
FIG. 3: Correlation for hypomethylated (A, $R^2=0.60$) and hypermethylated (B, $R^2=0.85$) probes in respiratory allergy cases as compared to healthy individuals between blood and saliva samples.
Figure 4:
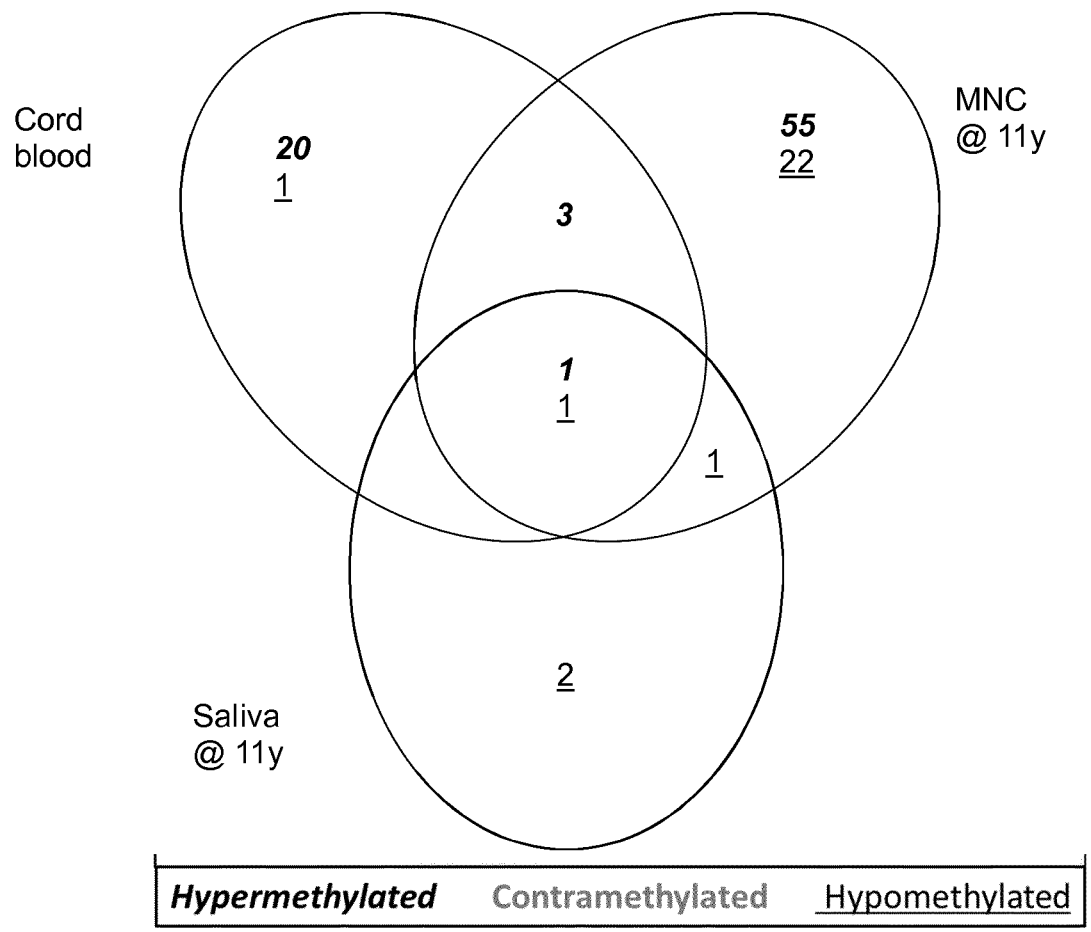
FIG. 4: Identification of differentially methylated regions (DMRs) between respiratory allergy cases and healthy controls in blood, cord blood and saliva samples. 2 identified DMRs were in common in cord blood, blood (mononuclear cell fraction, at 11 years of age) and saliva (at 11 years of age), of which one was hypomethylated (the corresponding gene plays a role in phagocytosis), and one was hypermethylated (the corresponding gene plays a role in IL4 signalling).

There were no significant differences in methylation of individual CpG sites. Though, using the Comb-p tool to identify DMR (selection criterium $P_{Adj}$<0.05) revealed 83 DMR between respiratory allergy cases and healthy individuals as detected in peripheral blood (Table 3, FIG. 3), and in saliva, 5 DMR between respiratory allergy cases and healthy individuals were identified (Table 4, FIG. 3). Of the identified DMR 3 were common between blood and saliva (FIG. 3).

TABLE 3

Differentially methylated regions between RA cases and healthy individuals in blood samples.

| Chromosomal position | Corresponding gene | Hyper(+) or Hypo (−) methylation |
|---|---|---|
| chr6: 32554480-32555411 | HLA-DRB1 | − |
| chr13: 100217961-100218927 | TM9SF2 | − |
| chr6: 32427750-32427898 | HLA-DRA | − |
| chr4: 81117646-81119473 | PRDM8 | − |
| chr2: 242801251-242802192 | PDCD1 | − |
| chr21: 47845609-47846235 | PCNT | − |
| chr1: 25291384-25292274 | RUNX3 | − |
| chr12: 133186598-133187452 | LRCOL1 | − |
| chr16: 22103595-22104151 | VWA3A | − |
| chr2: 242811148-242811962 | RTP5 | − |
| chr13: 110385517-110386267 | LINC00676 | − |
| chr9: 139552715-139553319 | EGFL7 | − |
| chr19: 18260329-18261134 | MAST3 | − |
| chr6: 106545983-106546824 | PRDM1 | − |
| chr16: 8806358-8807043 | ABAT | − |
| chr1: 212738303-212739113 | ATF3 | − |
| chr15: 72581568-72582316 | CELF6 | − |
| chr19: 50059749-50060306 | NOSIP | − |
| chr10: 94820085-94821085 | CYP26C1 | − |
| chr11: 691456-693032 | DEAF1 | − |
| chr4: 184908253-184909018 | STOX2 | − |
| chr3: 10332169-10333655 | GHRL; GHRL; GHRLOS; GHRL; GHRL | − |
| chr11: 698200-698760 | TMEM80 | − |
| chr2: 1792630-1793435 | MYT1L | − |
| chr6: 49681177-49681774 | CRISP2 | + |
| chr17: 76491988-76492566 | DNAH17; DNAH17-AS1 | + |
| chr1: 1888281-1889213 | CFAP74 | + |
| chr15: 22979751-22979826 | CYFIP1 | + |
| chr10: 670786-671628 | DIP2C | + |
| chr18: 61669939-61670413 | SERPINB8 | + |
| chr18: 60051869-60052464 | TNFRSF11A | + |
| chr7: 2150533-2151788 | MAD1L1 | + |
| chr5: 23506737-23507752 | PRDM9 | + |
| chr1: 10709184-10710134 | CASZ1 | + |
| chr1: 45190261-45191110 | C1orf228 | + |
| chr2: 11679604-11680144 | GREB1 | + |
| chr2: 51254822-51255627 | NRXN1 | + |
| chr13: 47471263-47472429 | HTR2A | + |
| chr10: 13424850-13425688 | SEPHS1 | + |
| chr1: 201618900-201619900 | NAV1 | + |
| chr13: 113120944-113121958 | TUBGCP3 | + |
| chr12: 41221638-41221855 | CNTN1 | + |
| chr16: 66613052-66613970 | CMTM2 | + |
| chr3: 146261940-146262761 | PLSCR1 | + |
| chr20: 30224894-30226046 | COX4I2 | + |
| chr8: 1900352-1900992 | ARHGEF10 | + |
| chr11: 68924576-68925191 | LOC338694 | + |
| chr19: 57349678-57350846 | PEG3; ZIM2 | + |
| chr17: 42431108-42432046 | FAM171A2 | + |
| chr2: 80527010-80527798 | CTNNA2 | + |
| chr9: 73736451-73737300 | TRPM3 | + |
| chr7: 56515509-56516504 | LOC650226 | + |
| chr12: 54763080-54764371 | ZNF385A; LOC102724050 | + |
| chr7: 16890430-16891079 | AGR3 | + |
| chr20: 30618873-30619244 | CCM2L | + |
| chr7: 48129796-48130197 | UPP1 | + |
| chr15: 40268420-40269214 | EIF2AK4 | + |
| chr14: 101618193-101618406 | MEG9 | + |
| chr10: 27702527-27703547 | PTCHD3 | + |
| chr11: 102638431-102638778 | MMP10 | + |
| chr2: 132201776-132203256 | LOC401010; RNU6-81P | + |
| chr4: 4863677-4864902 | MSX1 | + |
| chr6: 95220698-95221182 | TSG1 | + |
| chr21: 15645648-15646635 | ABCC13 | + |
| chr1: 149148207-149149691 | NBPF25P | + |
| chr1: 230414986-230416101 | GALNT2 | + |
| chr6: 33872205-33872861 | MIR7159 | + |
| chr19: 23945640-23946205 | RPSAP58 | + |

TABLE 3-continued

Differentially methylated regions between RA cases and healthy individuals in blood samples.

| Chromosomal position | Corresponding gene | Hyper(+) or Hypo (−) methylation |
|---|---|---|
| chr1: 153599478-153600156 | S100A13 | + |
| chr12: 132670343-132671672 | GALNT9 | + |
| chr14: 105318278-105318494 | CEP170B | + |
| chr4: 190938437-190940723 | FRG2 | + |
| chr10: 134407872-134407942 | INPP5A | + |
| chr3: 14338920-14339700 | LINC01267 | + |
| chr2: 115419536-115420260 | DPP10 | + |
| chr8: 2585665-2586911 | LOC101927815 | + |
| chr5: 126408755-126409573 | C5orf63 | + |
| chr17: 1507642-1508609 | SLC43A2 | + |
| chr7: 101398151-101398184 | CUX1 | + |
| chr15: 67355496-67356942 | SMAD3 | + |
| chr2: 121496874-121499710 | GLI2 | + |
| chr19: 43709653-43710277 | PSG4 | + |
| chr1: 205818667-205819609 | PM20D1 | + |

TABLE 4

Differentially methylated regions between RA cases and healthy individuals in saliva samples.

| Chromosomal position | Corresponding gene | Hyper(+) or Hypo (−) methylation |
|---|---|---|
| chr13: 100217961-100219013 | TM9SF2 | − |
| chr6: 32427750-32427898 | HLA-DRA | − |
| chr17: 43221219-43221807 | ACBD4 | − |
| chr4: 6728798-6729199 | BLOC1S4 | − |
| chr2: 121497333-121498812 | GLI2 | + |

Example 3: Discovery of Predictive Epigenetic Markers

Materials and Methods

The raw data obtained in Example 2 for cord blood were further processed and analyzed as described in Example 2 for identifying predictive epigenetic markers.

Results

In cord blood, 26 differently methylated regions (DMR) between respiratory allergy cases and healthy individuals were identified (Table 5, FIG. 3), of which 2 were also identified in blood and saliva samples at 11 years of age (FIG. 3).

TABLE 5

Differentially methylated regions between RA cases and healthy individuals in cord blood.

| Chromosomal position | Corresponding gene | Hyper(+) or Hypo (−) methylation |
|---|---|---|
| chr10: 8088800-8089733 | GATA3-AS1 | + |
| chr10: 42862977-42863594 | LOC441666 | + |
| chr10: 42971208-42971732 | LINC00839 | + |
| chr10: 101287380-101287846 | LINC01475 | + |
| chr10: 135341024-135342936 | CYP2E1 | + |
| chr11: 123430574-123431162 | GRAMD1B | + |
| chr12: 31271782-31272119 | DDX11 | + |
| chr13: 100217961-100219013 | TM9SF2 | − |
| chr15: 53093006-53093509 | ONECUT1 | + |
| chr16: 67997857-67998246 | SLC12A4 | + |
| chr17: 56565285-56565644 | HSF5 | + |
| chr17: 78851148-78851503 | RPTOR | − |
| chr18: 77917614-77918142 | PARD6G; PARD6G-AS1 | + |
| chr2: 27665016-27665711 | NRBP1; KRTCAP3 | + |
| chr2: 121496397-121499363 | GLI2 | + |
| chr20: 32255051-32256071 | NECAB3; ACTL10 | + |
| chr20: 60860732-60860984 | OSBPL2 | + |
| chr3: 30936069-30936531 | GADL1 | + |
| chr5: 80528608-80529340 | CKMT2; RNU5E-1; RNU5D-1 | + |
| chr5: 126408755-126409573 | C5orf63 | + |
| chr6: 28226884-28227482 | NKAPL | + |
| chr6: 33280198-33280571 | TAPBP | + |
| chr7: 48129443-48130197 | UPP1 | + |
| chr7: 94953652-94954202 | PON1 | + |
| chr7: 127880931-127881440 | LEP | + |
| chr8: 2585234-2586225 | LOC101927815 | + |

What is claimed is:

1. An in vitro method for determining DNA methylation status, comprising:
   (a) obtaining a saliva test sample from a patient showing one or more clinical symptoms of the respiratory allergy;
   (b) isolating a genomic DNA from said saliva test sample;
   (c) treating said isolated genomic DNA with bisulfite in order to convert non-methylated cytosine bases into uracil bases; and
   (d) detecting a hypermethylation of a GLI2 gene and a hypomethylation of a TM9SF2 gene in the treated genomic DNA by performing a methylation specific PCR.

2. The method according to claim 1, wherein said detecting is conducted by detecting the hypermethylation of the GLI2 gene on the chromosome 2, and detecting a hypomethylation of a TM9SF2 gene on a chromosome 13, and detecting a hypomethylation of a HLA-DRA on a chromosome 6; wherein the chromosome 2, 13, and chromosome 6 are obtained from said saliva test sample.

3. The method according to claim 1 wherein said detecting is conducted by detecting the hypermethylation of the GLI2 gene on the chromosome 2, and detecting a hypomethylation of a TM9SF2 gene on a chromosome 13, a HLA-DRA on a chromosome 6, an ACBD4 gene on a chromosome 17 or a BLOC1S4 gene on a chromosome 4, wherein the chromosome 2, chromosome 13, chromosome 6, chromosome 17 and chromosome 4 are obtained from said saliva test sample.

4. The method according to claim 1, wherein said (d) detecting is conducted by detecting the hypermethylation of between 2 and 20 CpG dinucleotides located in said GLI2 gene.

* * * * *